(12) United States Patent
LeBoeuf et al.

(10) Patent No.: US 11,058,304 B2
(45) Date of Patent: Jul. 13, 2021

(54) METHODS OF CONTROLLING BIOMETRIC PARAMETERS VIA MUSICAL AUDIO

(71) Applicant: Valencell, Inc., Raleigh, NC (US)

(72) Inventors: Steven Francis LeBoeuf, Raleigh, NC (US); Jesse Berkley Tucker, Youngsville, NC (US); Michael Edward Aumer, Raleigh, NC (US); Lawrence Christopher Eschbach, Louisburg, NC (US); Ryan D. Hodges, Raleigh, NC (US); Manoj Patwardhan, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 416 days.

(21) Appl. No.: 15/744,642

(22) PCT Filed: Jul. 12, 2016

(86) PCT No.: PCT/US2016/041842
§ 371 (c)(1),
(2) Date: Jan. 12, 2018

(87) PCT Pub. No.: WO2017/011431
PCT Pub. Date: Jan. 19, 2017

(65) Prior Publication Data
US 2018/0220901 A1 Aug. 9, 2018

Related U.S. Application Data

(60) Provisional application No. 62/274,463, filed on Jan. 4, 2016, provisional application No. 62/192,683, filed on Jul. 15, 2015.

(51) Int. Cl.
*A61B 5/0205* (2006.01)
*A61B 5/024* (2006.01)
(Continued)

(52) U.S. Cl.
CPC ........ *A61B 5/02055* (2013.01); *A61B 5/0022* (2013.01); *A61B 5/024* (2013.01);
(Continued)

(58) Field of Classification Search
CPC ... A61B 5/6831; A61B 5/7246; A61B 5/7415; A61B 5/0022; A61B 5/0456;
(Continued)

(56) References Cited

U.S. PATENT DOCUMENTS 8,647,270 B2  2/2014  LeBoeuf et al.
8,652,040 B2  2/2014  LeBoeuf et al.
(Continued)

*Primary Examiner* — Navin Natnithithadha
*Assistant Examiner* — Sunita Reddy
(74) *Attorney, Agent, or Firm* — Myers Bigel, P.A.

(57) ABSTRACT

A method of controlling a biometric parameter, such as heart rate and/or breathing rate, of a subject engaged in an activity includes sensing the biometric parameter via a monitoring device worn by the subject, determining frequency characteristics of the biometric parameter, and presenting to the subject musical audio having a tempo correlated to the frequency characteristics of the biometric parameter. The tempo of the musical audio presented to the subject may be changed in order to cause a change in the biometric parameter. A method of modulating heart rate of a subject engaged in an activity includes sensing a breathing rate of the subject via a monitoring device worn by the subject, and then presenting to the subject musical audio having a tempo selected to change the breathing rate by an amount sufficient to cause a change in the heart rate.

6 Claims, 17 Drawing Sheets

(51) Int. Cl.
  *A61B 5/00* (2006.01)
  *A61B 5/08* (2006.01)
  *A61B 5/11* (2006.01)
  *A61B 5/352* (2021.01)

(52) U.S. Cl.
  CPC .......... *A61B 5/0816* (2013.01); *A61B 5/6817* (2013.01); *A61B 5/6831* (2013.01); *A61B 5/7246* (2013.01); *A61B 5/7415* (2013.01); *A61B 5/1118* (2013.01); *A61B 5/352* (2021.01); *A61B 2503/10* (2013.01)

(58) Field of Classification Search
  CPC . A61B 5/024; A61B 2503/10; A61B 5/02055; A61B 5/0816; A61B 5/6817; A61B 5/1118
  USPC ....................................................... 600/26–28
  See application file for complete search history.

(56) References Cited

U.S. PATENT DOCUMENTS

| | | | |
|---|---|---|---|
| 8,700,111 B2 | 4/2014 | LeBoeuf et al. | |
| 8,788,002 B2 | 7/2014 | LeBoeuf et al. | |
| 8,886,269 B2 | 11/2014 | LeBoeuf et al. | |
| 8,929,965 B2 | 1/2015 | LeBoeuf et al. | |
| 2004/0116784 A1* | 6/2004 | Gavish | A61B 5/02007 600/300 |
| 2006/0241510 A1* | 10/2006 | Halperin | A61B 5/113 600/534 |
| 2008/0146890 A1* | 6/2008 | LeBoeuf | A61B 5/4839 600/300 |
| 2008/0146892 A1* | 6/2008 | LeBoeuf | G16H 50/30 600/300 |
| 2008/0214903 A1* | 9/2008 | Orbach | A61B 5/486 600/301 |
| 2009/0112071 A1* | 4/2009 | LeBoeuf | A61B 5/02116 600/301 |
| 2010/0217098 A1* | 8/2010 | LeBoeuf | A61B 5/002 600/301 |
| 2010/0217099 A1* | 8/2010 | LeBoeuf | A61B 5/0024 600/301 |
| 2010/0217100 A1* | 8/2010 | LeBoeuf | A61B 5/11 600/301 |
| 2011/0106627 A1* | 5/2011 | LeBoeuf | G16H 50/30 705/14.66 |
| 2013/0171599 A1* | 7/2013 | Bleich | A61B 5/0456 434/247 |
| 2014/0031638 A1* | 1/2014 | Jung | A61B 5/4848 600/301 |
| 2014/0114147 A1* | 4/2014 | Romesburg | A61B 5/04017 600/301 |
| 2014/0128690 A1* | 5/2014 | LeBoeuf | A61B 5/02055 600/301 |
| 2014/0140567 A1* | 5/2014 | LeBoeuf | A61B 5/0408 381/381 |
| 2014/0155708 A1* | 6/2014 | Petersen | A61B 5/02055 600/301 |
| 2014/0275854 A1* | 9/2014 | Venkatraman | A61B 5/721 600/301 |
| 2014/0277241 A1* | 9/2014 | Bleich | A61N 1/36585 607/18 |
| 2015/0080746 A1* | 3/2015 | Bleich | A63B 69/0028 600/479 |
| 2015/0313475 A1* | 11/2015 | Benson | A61B 5/6893 297/217.3 |
| 2015/0313484 A1* | 11/2015 | Burg | A61B 5/113 600/301 |
| 2015/0335288 A1* | 11/2015 | Toth | A61B 5/6833 600/373 |

* cited by examiner

| PHYSIOLOGICAL ASSESSMENT PARAMETER | POTENTIAL PHYSIOLOGICAL ASSESSMENT(S) |
|---|---|
| SD1, SD2 | GENERALLY, SD1 AND SD2 MAY BE DIRECTLY RELATED TO OVERALL HEALTH AND LOWER STRESS, AND A HIGHER THAN AVERAGE SD1 AND SD2 IS DESIRABLE. SD1 IS GENERALLY RELATED TO PARASYMPATHETIC ACTIVITY (TONE) AND 1/SD2 IS GENERALLY RELATED TO SYMPATHETIC ACTIVITY (TONE). |
| SD1/SD2 | AN SD1/SD2 RATIO THAT IS MUCH HIGHER OR MUCH LOWER THAN AVERAGE MAY INDICATE DISEASE OF THE HEART, NERVOUS SYSTEM, DIGESTIVE SYSTEM, OR MUSCLES. AN UNHEALTHY (ABNORMAL) SD1/SD2 RATIO IN CONTEXT OF A HEALTHY (NORMAL) SD1 AND SD2 VALUE MAY IDENTIFY THE PRESENCE OF SPECIFIC DISEASE CONDITIONS. |
| $1/(SD1*SD2)$ | $1/(SD1*SD2)$ REPRESENTS THE RATIO OF SYMPATHETIC TO PARASYMPATHETIC ACTIVITY (TONE). A VALUE THAT IS MUCH HIGHER OR MUCH LOWER THAN AVERAGE MAY INDICATE A LACK OF BALANCE IN THE AUTONOMIC NERVOUS SYSTEM. |
| $SD1_{CB}/SD1_{UCB}$ | AN $SD1_{CB}/SD1_{UCB}$ RATIO OF ~1 SUGGESTS A LACK OF PARASYMPATHETIC RESPONSIVENESS TO CONTROLLED BREATHING; A HIGHER OR LOWER THAN $SD1_{CB}/SD1_{UCB}$ RATIO MAY BE A SIGN OF DISEASE. |
| $SD2_{CB}/SD2_{UCB}$ | AN $SD2_{CB}/SD2_{UCB}$ RATIO OF ~1 SUGGESTS A LACK OF SYMPATHETIC RESPONSIVENESS TO CONTROLLED BREATHING; A HIGHER OR LOWER THAN AVERAGE $SD2_{CB}/SD2_{UCB}$ RATIO MAY BE A SIGN OF DISEASE; THE $SD2_{CB}/SD2_{UC}$ SHOULD BE >1 FOR THE CASE WHERE CONTROLLED BREATHING IS ABLE TO REDUCE STRESS FOR THE USER. |
| $(SD1_{CB}/SD2_{CB})/(SD1_{UCB}/SD2_{UCB})$ | AN $(SD1_{CB}/SD2_{CB})/(SD1_{UCB}/SD2_{UCB})$ RATIO OF ~1 SUGGESTS THAT THE SUBJECT IS UNABLE TO REACH A STATE OF RELAXATION WITH CONTROLLED BREATHING, WHICH MAY BE A SIGN OF CHRONIC STRESS. |
| $(SD1_{UCB}*SD2_{UCB})/(SD1_{CB}*SD2_{CB})$ | $(SD1_{UCB}*SD2_{UCB})/(SD1_{CB}*SD2_{CB})$ REPRESENTS THE RATIO OF AUTONOMIC BALANCE BETWEEN STATES OF CONTROLLED BREATHING AND UNCONTROLLED BREATHING. A RATIO MUCH HIGHER OR MUCH LOWER THAN AVERAGE, OR A RATIO MUCH HIGHER OR LOWER THAN ~1 MAY SUGGEST THAT THE USER SUFFERS FROM STRESS-RELATED HEALTH CONDITIONS. |
| $SDNN_{CB}/SDNN_{UCB}$ | IN HEALTHY SUBJECTS, THE $SDNN_{CB}/SDNN_{UCB}$ SHOULD BE >1. |

FIG. 24

METHODS OF CONTROLLING BIOMETRIC PARAMETERS VIA MUSICAL AUDIO

RELATED APPLICATIONS

This application is a 35 U.S.C. § 371 national stage application of PCT Application No. PCT/US2016/041842, which itself claims the benefit of and priority to U.S. Provisional Patent Application No. 62/192,683 filed Jul. 15, 2015, and U.S. Provisional Patent Application No. 62/274,463 filed Jan. 4, 2016, the disclosures of all of which are incorporated herein by reference as if set forth in their entireties. The above-referenced PCT International Application was published in the English language as International Publication No. WO 2017/011431 A2 on Jan. 19, 2017.

FIELD OF THE INVENTION

The present invention relates generally to monitoring devices and, more particularly, to monitoring devices for measuring physiological information.

BACKGROUND OF THE INVENTION

Wearable devices capable of monitoring physiological information, such as heart rate, are increasingly being used. These devices come in various form factors, including devices configured to be worn at the ear or at other locations of the body. U.S. Pat. Nos. 8,652,040, 8,700,111, 8,647,270, 8,788,002, 8,886,269, and 8,929,965, which are incorporated herein by reference in their entireties, describe various wearable devices configured to monitor physiological information, including headsets, earbuds, and wrist bands. Physiological information obtained from a subject can be used to generate various types of health and fitness assessments of the subject. For example, using a photoplethysmography (PPG) sensor incorporated into a wearable monitoring device, blood flow information can be measured during daily activities of a subject and this information can be used to generate assessments, such as maximum oxygen consumption $VO_2$max, total energy expenditure (TEE), etc.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

Embodiments of the present invention can facilitate identifying musical audio that can improve a person's exercise training, and can facilitate identifying the best biometric parameters for optimizing the person's exercise training. For example, embodiments of the present invention can be used to study a person's biometric correlations with music while exercising and listening to music to learn how music tempo relates to a controllable biometric parameter and then learn how to directly control that biometric as a means of indirectly controlling another biometric. Moreover, embodiments of the present invention can be used to help a person learn how to minimize heart rate (HR) for a given workload and thus improve endurance during exercise (i.e., running, cycling, swimming, etc). Alternately, the person can learn how to maximize HR for a given workload and thus increase energy expenditure during exercise.

According to some embodiments of the present invention, a method of controlling a biometric parameter of a subject engaged in an activity includes sensing the biometric parameter via a monitoring device worn by the subject, determining frequency characteristics of the biometric parameter, and presenting to the subject musical audio having a tempo correlated to the frequency characteristics of the biometric parameter. In some embodiments, the biometric parameter is breathing rate, and musical audio having a tempo correlated to frequency characteristics of the breathing rate is presented to the subject. In some embodiments, the biometric parameter is heart rate, and musical audio having a tempo correlated to frequency characteristics of the heart rate is presented to the subject.

In some embodiments, the tempo of musical audio presented to the subject can be changed in order to cause a change in the biometric parameter. For example, if the biometric parameter is breathing rate, the tempo of the musical audio can be changed to cause a change in the breathing rate of the subject. If the biometric parameter is heart rate, the tempo of the musical audio can be changed to cause a change in the heart rate of the subject.

In some embodiments, the monitoring device is configured to be positioned at or within an ear of the subject, and in other embodiments, the monitoring device is configured to be secured to an appendage of the subject or at a different location of the body of the subject. In some embodiments, the monitoring device is integrated within or otherwise associated with clothing worn by the subject.

According to other embodiments of the present invention, a method of controlling a biometric parameter of a subject engaged in an activity includes sensing the biometric parameter via a monitoring device worn by the subject (e.g., a device positioned at or within an ear of the subject, secured to an appendage of the subject, integrated within or otherwise associated with clothing worn by the subject, etc.) as musical audio is presented to the subject. Characteristics of the musical audio are analyzed in context with frequency characteristics of the biometric parameter. One or more correlations between the musical audio characteristics and the frequency characteristics of the biometric parameter are identified, and then additional musical audio is selected for subsequent presentation to the subject based on the one or more correlations. Selecting additional musical audio may include selecting musical audio having a tempo correlated to the frequency characteristics of the biometric parameter. For example, if the biometric parameter is breathing rate, additional musical audio having a tempo correlated to frequency characteristics of the breathing rate is selected and presented. If the biometric parameter is heart rate, additional musical audio having a tempo correlated to frequency characteristics of the heart rate is selected and presented.

In some embodiments, the tempo of the additional musical audio presented to the subject can be changed in order to cause a change in the biometric parameter.

In some embodiments, selecting additional musical audio for presentation to the subject based on the one or more correlations includes selecting a playlist of additional musical audio.

According to other embodiments of the present invention, a method of presenting musical audio to a subject engaged in an activity includes sensing physiological information from the subject via a monitoring device worn by the subject (e.g., a device positioned at or within an ear of the subject, secured to an appendage of the subject, integrated within or otherwise associated with clothing worn by the subject, etc.), analyzing the physiological information to identify a natural body frequency of the subject, and then presenting musical audio to the subject that is in resonance with the natural body frequency and/or in resonance with a harmonic of the natural body frequency. In some embodiments, the physiological information includes breathing rate, RRi (R-R interval) and/or heart rate.

According to other embodiments of the present invention, a method of modulating heart rate of a subject engaged in an activity includes sensing a breathing rate of the subject via a monitoring device worn by the subject (e.g., a device positioned at or within an ear of the subject, secured to an appendage of the subject, integrated within or otherwise associated with clothing worn by the subject, etc.), and then presenting to the subject musical audio having a tempo selected to change the breathing rate by an amount sufficient to cause a change in the heart rate by a desired amount. In some embodiments, presenting to the subject musical audio having a tempo selected to change the breathing rate by an amount sufficient to cause a change in the heart rate may include presenting musical audio having a tempo selected to increase the breathing rate by an amount sufficient to cause an increase in the heart rate. Similarly, presenting to the subject musical audio having a tempo selected to change the breathing rate by an amount sufficient to cause a change in the heart rate may include presenting musical audio having a tempo selected to decrease the breathing rate by an amount sufficient to cause a decrease in the heart rate.

According to other embodiments of the present invention, a method of determining a ventilatory threshold of a subject engaged in an activity includes sensing heart rate information, breathing rate information, and motion information from the subject via a monitoring device worn by the subject (e.g., a device positioned at or within an ear of the subject, secured to an appendage of the subject, integrated within or otherwise associated with clothing worn by the subject, etc.). The heart rate and breathing rate information is analyzed to identify one or more points in time where the subject's heart rate increased at a steady subject workload. Ventilatory threshold is then identified as occurring at a point in time where a rapid increase in breathing rate lagged a rapid increase in heart rate.

According to other embodiments of the present invention, a method of determining body temperature of a subject engaged in an activity includes sensing heart rate information and motion information from the subject via a monitoring device worn by the subject (e.g., a device positioned at or within an ear of the subject, or secured to an appendage of the subject, etc.). The heart rate information is analyzed to identify one or more points in time where heart rate changed at a steady subject workload. The body temperature of the subject is then determined at each of the one or more points in time based on an amount of change in heart rate at each respective point in time.

According to other embodiments of the present invention, a method of controlling a physical activity parameter of a subject engaged in an activity includes sensing the physical activity parameter and a periodic biometric parameter via at least one monitoring device worn by the subject. Frequency characteristics of the activity parameter and biometric parameter are determined and audio feedback is provided to the subject to encourage the subject to maintain a frequency of the physical activity parameter such that the physical activity parameter and biometric parameter share a common fundamental frequency. In some embodiments, the physical activity parameter includes an exercise cadence and the biometric parameter includes heart rate and/or breathing rate.

According to other embodiments of the present invention, a method of generating a physiological assessment of a subject includes guiding the subject into a state of controlled breathing, sensing physical activity information via at least one monitoring device worn by the subject, sensing biometric information via the at least one monitoring device, processing the physical activity information and biometric information to generate a physiological assessment of the subject, and providing feedback to the subject related to the physiological assessment. The at least one monitoring device may include a PPG sensor, an ECG sensor, an auscultatory sensor, a piezoelectric sensor, a ballistogram sensor, or a bioimpedance sensor. A physiological assessment may include subject health status, subject physical fitness, subject physical stress status, and/or subject mental stress status.

Guiding the subject into a state of controlled breathing may include providing the subject with audible and/or visual instructions. In some embodiments, audible and/or visual instructions may be provided via a human being. In other embodiments, audible and/or visual instructions may be provided via an electronic device, such as a cell phone, television, computer, etc. Providing feedback to the subject related to the physiological assessment may include providing the subject with audible and/or visual feedback.

In some embodiments, sensing biometric information includes monitoring R-R interval in an electrocardiogram or photoplethysmogram of the subject. In some embodiments, sensing physical activity information includes sensing subject distance traveled, subject speed, subject acceleration, subject cadence, subject pace, or subject gait.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

FIG. 24 is a table of physiological assessment parameters and potential assessments, according to some embodiments of the present invention.

DETAILED DESCRIPTION

Figure 1:
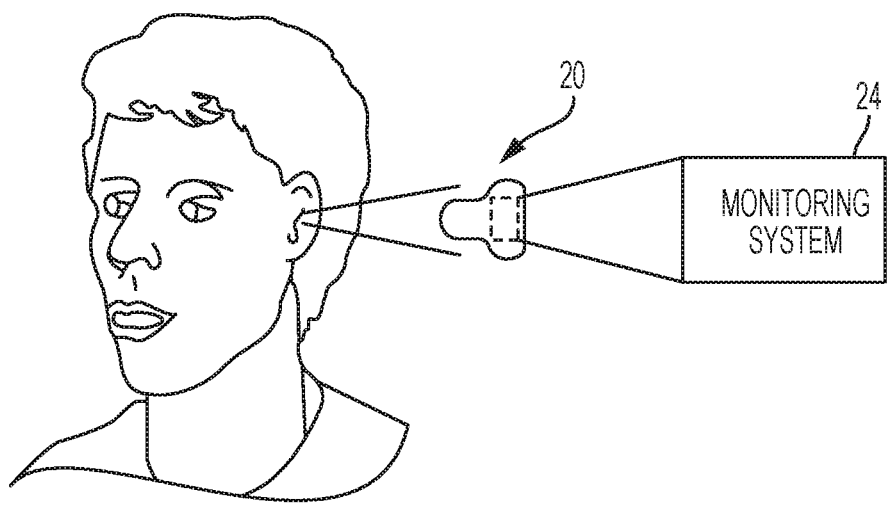
FIG. 1 illustrates an audio earbud capable of sensing physiological information from a person wearing the earbud.
Figure 2:
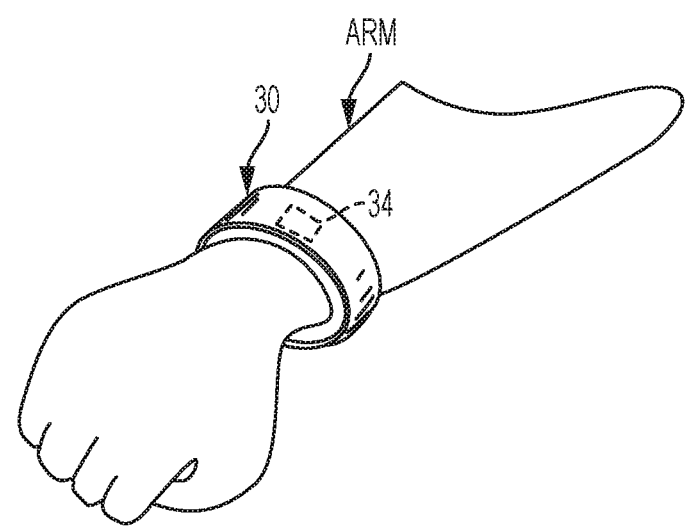
FIG. 2 illustrates a wrist band positioned around a wrist of a person, which may also be applied for wear at a limb or digit, and that includes a sensor module configured to sense physiological information from the person.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain components or features may be exaggerated for clarity. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "secured", "connected", "attached" or "coupled" to another feature or element, it can be directly secured, directly connected, attached or coupled to the other feature or element or intervening features or elements may be present. In contrast, when a feature or element is referred to as being "directly secured", "directly connected", "directly attached" or "directly coupled" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

As used herein, the term "and/or" includes any and all combinations of one or more of the associated listed items and may be abbreviated as "/".

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features or elements, these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary more or less, for example by +/−20%, +/−10%, +/−5%, +/−1%, +/−0.5%, +/−0.1%, etc.

The terms "sensor", "sensing element", and "sensor module", as used herein, are interchangeable and refer to a sensor element or group of sensor elements that may be utilized to sense information, such as information (e.g., physiological information, body motion, etc.) from the body of a subject and/or environmental information in a vicinity of the subject. A sensor/sensing element/sensor module may comprise one or more of the following: a detector element, an emitter element, a processing element, optics, mechanical support, supporting circuitry, and the like. Both a single sensor element and a collection of sensor elements may be considered a sensor, a sensing element, or a sensor module.

The term "optical emitter", as used herein, may include a single optical emitter and/or a plurality of separate optical emitters that are associated with each other.

The term "optical detector", as used herein, may include a single optical detector and/or a plurality of separate optical detectors that are associated with each other.

The term "wearable sensor module", as used herein, refers to a sensor module configured to be worn on or near the body of a subject.

The terms "monitoring device" and "biometric monitoring device", as used herein, are interchangeable and include any type of device, article, or clothing that may be worn by and/or attached to a subject and that includes at least one sensor/sensing element/sensor module. Exemplary monitoring devices may be embodied in an earpiece, a headpiece, a finger clip, a digit (finger or toe) piece, a limb band (such as an arm band or leg band), an ankle band, a wrist band, a nose piece, a sensor patch, eyewear (such as glasses or shades), apparel (such as a shirt, hat, underwear, etc.), a mouthpiece or tooth piece, contact lenses, or the like.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "headset", as used herein, is intended to include any type of device or earpiece that may be attached to or near the ear (or ears) of a user and may have various configurations, without limitation. Headsets incorporating sensor modules, as described herein, may include mono headsets (a device having only one earbud, one earpiece, etc.) and stereo headsets (a device having two earbuds, two earpieces, etc.), true wireless headsets (having two wireless earpieces), earbuds, hearing aids, ear jewelry, face masks, headbands, glasses or eyewear, and the like. In some embodiments, the term "headset" may include broadly headset elements that are not located on the head but are associated with the headset. For example, in a "medallion" style wireless headset, where the medallion comprises the wireless electronics and the headphones are plugged into or hard-wired into the medallion, the wearable medallion would be considered part of the headset as a whole. Similarly, in some cases, if a mobile phone or other mobile device is intimately associated with a plugged-in headphone, then the term "headset" may refer to the headphone-mobile device combination. The terms "headset" and "earphone", as used herein, are interchangeable.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature.

The term "body" refers to the body of a subject (human or animal) that may wear a monitoring device, according to embodiments of the present invention.

The term "processor" is used broadly to refer to a signal processor or computing system or processing or computing method which may be localized or distributed. For example, a localized signal processor may comprise one or more signal processors or processing methods localized to a general location, such as to a wearable device. Examples of such wearable devices may comprise an earpiece, a headpiece, a finger clip, a digit (finger or toe) piece, a limb band (such as an arm band or leg band), an ankle band, a wrist band, a nose piece, a sensor patch, eyewear (such as glasses or shades), apparel (such as a shirt, hat, underwear, etc.), a mouthpiece or tooth piece, contact lenses, or the like. Examples of a distributed processor comprise "the cloud", the internet, a remote database, a remote processor computer, a plurality of remote processors or computers in communication with each other, or the like, or processing methods distributed amongst one or more of these elements. The key difference is that a distributed processor may include delocalized elements, whereas a localized processor may work independently of a distributed processing system. As a specific example, microprocessors, microcontrollers, ASICs (application specific integrated circuits), analog processing circuitry, or digital signal processors are a few non-limiting examples of physical signal processors that may be found in wearable devices.

The term "remote" does not necessarily mean that a remote device is a wireless device or that it is a long distance away from a device in communication therewith. Rather, the term "remote" is intended to reference a device or system that is distinct from another device or system or that is not substantially reliant on another device or system for core functionality. For example, a computer wired to a wearable device may be considered a remote device, as the two devices are distinct and/or not substantially reliant on each other for core functionality. However, any wireless device (such as a portable device, for example) or system (such as a remote database for example) is considered remote to any other wireless device or system.

The terms "music" and "musical audio", as used herein, are interchangeable and refer to vocal and/or instrumental sounds that can be played or otherwise presented to a person, for example, via speakers, earbuds, etc.

The term "tempo", as used herein, refers to the speed of the rhythm at which a composition of music is played. Conventionally, tempo is measured according to beats per minute. For example, according to some conventions, a very fast tempo, prestissimo, has between 200 and 208 beats per minute, presto has 168 to 200 beats per minute, allegro has between 120 and 168 beats per minute, moderato has 108 to 120 beats per minute, andante has 76 to 108 beats per minute, adagio has 66 to 76 beats per minute, larghetto has 60 to 66 beats per minute, and largo has 40 to 60 beats per minute.

The term "cadence", as used herein, refers to the frequency or repetition rate of an activity. During running or walking, for example, one's primary cadence may be their running or walking cadence (their footstep rate). During weightlifting, one's primary cadence may be their weightlifting cadence (their "rep rate" or repetition rate). Generally speaking, "exercise cadence" refers to the primary cadence of a particular exercise. It should be noted that some exercises may be characterized by actions that involve more than one cadence—for example, during swimming, one may have an arm-stroke cadence which is different than the cadence of their leg motion. Thus, in some cases, more than one exercise cadence may be required to accurately assess one's workload.

The term "workload", as used herein, refers to the amount of work required to perform a task, for example, the amount of work required by a person to perform a task (e.g., running, swimming, exercising, etc.). Workload is typically measured in terms of power (watts) or total energy (joules or calories burned). However, workload may be estimated by measuring or estimating a cadence, speed, or distance traveled by someone and applying various assumptions to correlate distance or exercise cadence with work performed. For example, a constant workload may be associated with running at a constant speed on a flat surface (as altitude changes must be factored at a constant speed, since running up a hill is more work than running down a hill for the same speed). Other indirect measurements, such as measurements of heart rate, respiration rate, etc. can be used to estimate workload. Combinational models of biometric parameters (heart rate, respiration rate, blood pressure, and the like) and physical activity parameters (distance traveled, speed, acceleration, and the like) may also be applied towards indirectly measuring (estimating) workload. However, it should be noted that using heart rate to estimate workload can be deceiving, as heart rate may increase with internal body changes (such as temperature changes, digestion, exhaustion, and the like) independently of true physical workload. Examples of direct measurements of workload may include treadmill distance monitoring, cadence monitoring, power metering, video recording, or the like.

Cadence monitoring may be particularly useful for a person wearing a wearable device, as cadence may be measured by an accelerometer. In a particular embodiment, an assessment of workload may be approximated by measuring a user's cadence. In another embodiment, an assessment of workload may be generated by measuring the user cadence of a physical activity by multiplying the user cadence by a scaler value "m" and adding a constant "b" in the form of a linear equation, where the "m" value is an experimentally derived slope relating a user's cadence to energy expenditure and the "b" value is related to an estimate of REE (resting energy expenditure).

The terms "energy expenditure" and "total calories burned", as used herein, are interchangeable. It should be understood that energy expenditure and workload are not necessarily equal, as energy can be expended at rest due to homeostasis or fidgeting, which is not considered as a workload. As with workload, energy expenditure may be indirectly measured (estimated) via physiological models, i.e., by applying models for heart rate vs. energy expenditure or accelerometry measurements vs. energy expenditure, or combination models of heart rate and accelerometry. However, it should be noted that using heart rate to estimate energy expenditure also may be deceiving, as heart rate may reach a physical limit (maximum possible heart rate) during intense exercise even when energy expenditure is increasing. Examples of direct measurements of energy expenditure may include gas exchange analysis, doubly-labeled water assays, metabolic chamber monitoring, or the like.

The terms "respiration rate" and "breathing rate", as used herein, are interchangeable.

The terms "heart rate" and "pulse rate", as used herein, are interchangeable.

The term "RRi" refers to "R-R interval" in the electrocardiogram or photoplethysmogram of a person. Generally, where heart rate is used in embodiments of the present invention, RRi may also be applied in a similar manner. However, RRi and heart rate are generally related in an inverse fashion, such that 1/RRi=instantaneous heart rate.

The term "HRV" refers to "heart rate variability" or "R-R variability", which is a statistical representation of a group of consecutive R-R intervals or N-N intervals (beat-to-beat intervals between consecutive heart beats). The types of statistics performed to generate an HRV value can be quite numerous and broad. In general, a variety of different time-domain and/or frequency domain statistics on heart beat intervals can be described as different HRV values. As one specific example of HRV, 2- or 5-minutes worth of R-R intervals may be processed to determine the mean and standard deviation (SDNN), which is a representation of HRV. In general, the higher the SDNN for a group of R-R intervals collected from a person, the more relaxed, physically fit, or healthy that person may be. N-N intervals may be collected via photoplethysmograms (PPG), electrocardiograms (ECG), blood pressure pulses, ballistocardiograms (BCG), and the like.

The term "natural body frequency", as used herein, refers to a resonant frequency of the body or other characteristic frequency of the body where some sort of resonance may occur. For example, resonance between breathing rate and heart rate may be a natural body frequency. Resonance can refer to the case where heart rate and respiration rate share a fundamental frequency (they are harmonics of the same fundamental frequency) or it can refer to the case where the heart rate variability (HRV) is at a maximum. As another example, a resonance between someone's running or walking cadence (or more broadly their exercise cadence) and heart rate (or other periodic vital sign) may be a natural body frequency. In another example, the mechanical structure of the body (in terms of springs, damping, and the like) may have a mechanical resonance frequency. In another example, the periodic neurological processing of the human body, or homeostasis, may be characterized by a natural frequency.

The term "fundamental frequency", as used herein, refers to the lowest frequency of a periodic waveform. For example, breathing rate and heart rate may resonate with each other when they share a fundamental frequency, such as when heart rate is 6× that of the breathing rate.

Various biometric parameters and activity parameters may be described herein by using the name of the parameter (such as "heart rate", VO₂max, and the like). Generally speaking, these names may refer to instantaneous values, averaged values, or some other processing of the associated parameter(s). For example, a breathing rate of 14 BPM (breaths per minute) may refer to an instantaneous measurement or an averaged measurement (for example, an average breathing rate of 14 BPM as averaged over 5 minutes). Unless "instantaneous", "average", or some other adjective is used to describe the parameter, it should not be assumed that there is a limitation with respect to the processing of the parameter.

The term "periodic biometric parameter", as used herein, refers to a biometric parameter that is derived from a periodic process in the body of a subject such that it is characterized by a rate or frequency, such as heart rate, breathing rate, homeostasis, RRi, neurological functioning, sleep cycles, and the like.

In the following figures, various monitoring devices will be illustrated and described for attachment to the ear or an appendage of the human body. However, it is to be understood that embodiments of the present invention are not limited to those worn by humans.

The ear is an ideal location for wearable health and environmental monitors. The ear is a relatively immobile platform that does not obstruct a person's movement or vision. Monitoring devices located at an ear have, for example, access to the inner-ear canal and tympanic membrane (for measuring core body temperature), muscle tissue (for monitoring muscle tension), the pinna, earlobe, and elsewhere (for monitoring blood gas levels), the region behind the ear (for measuring skin temperature and galvanic skin response), and the internal carotid artery (for measuring cardiopulmonary functioning), etc. The ear is also at or near the point of exposure to: environmental breathable toxicants of interest (volatile organic compounds, pollution, etc.); noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion. Accurate sensing of photoplethysmograms and heart rate from the ear has been demonstrated in regions between the concha and anti-tragus locations of the outer ear, and elsewhere at the ear.

Optical coupling into the blood vessels of the ear may vary between individuals. As used herein, the term "coupling" refers to the interaction or communication between excitation energy (such as light) entering a region and the region itself. For example, one form of optical coupling may be the interaction between excitation light generated from within an optical sensor of an earbud (or other device positioned at or within an ear) and the blood vessels of the ear. In one embodiment, this interaction may involve excitation light entering the ear region and scattering from a blood vessel in the ear such that the temporal change in intensity of scattered light is proportional to a temporal change in blood flow within the blood vessel. Another form of optical coupling may be the interaction between excitation light generated by an optical emitter within an earbud and a light-guiding region of the earbud. Thus, an earbud with integrated light-guiding capabilities, wherein light can be guided to multiple and/or select regions along the earbud, can assure that each individual wearing the earbud will generate an optical signal related to blood flow through the blood vessels. Optical coupling of light to a particular ear region of one person may not yield photoplethysmographic signals for each person. Therefore, coupling light to multiple regions may assure that at least one blood-vessel-rich region will be interrogated for each person wearing an earbud. Coupling multiple regions of the ear to light may also be accomplished by diffusing light from a light source within an earbud.

Figure 3:
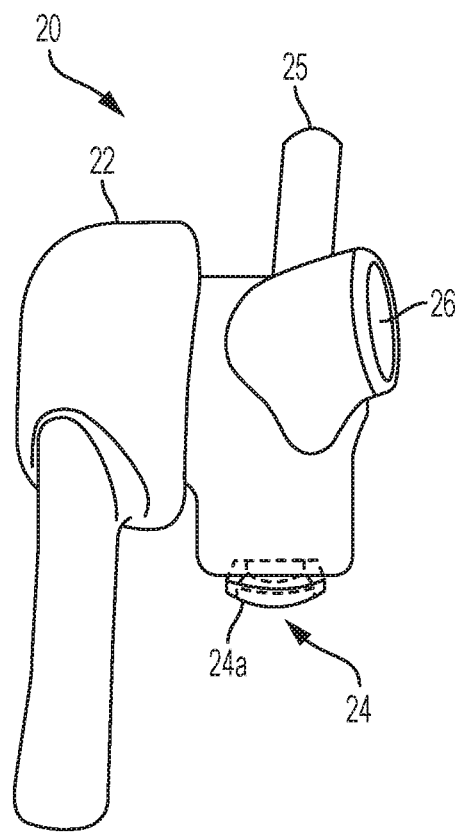
FIG. 3 illustrates an audio earbud capable of sensing physiological information from a person wearing the earbud.

FIGS. 1 and 3 illustrate audio earbud 20 capable of sensing physiological information and configured to be positioned within an ear of a subject, according to some embodiments of the present invention. The illustrated apparatus 20 of FIG. 3 includes an earpiece body or housing 22, a sensor module 24, a stabilizer 25 (optional), and a sound port 26. When positioned within the ear of a subject, the sensor module 24 has a region 24a configured to contact a selected area of the ear. The illustrated sensor region 24a may be contoured (i.e., is "form-fitted") to matingly engage a portion of the ear between the anti tragus and acoustic meatus, and the stabilizer is configured to engage the antihelix. However, monitoring devices in accordance with embodiments of the present invention can have sensor modules with one or more regions configured to engage various portions of the ear. Various types of device configured to be worn at or near the ear may be utilized in conjunction with embodiments of the present invention.

Figure 4A:
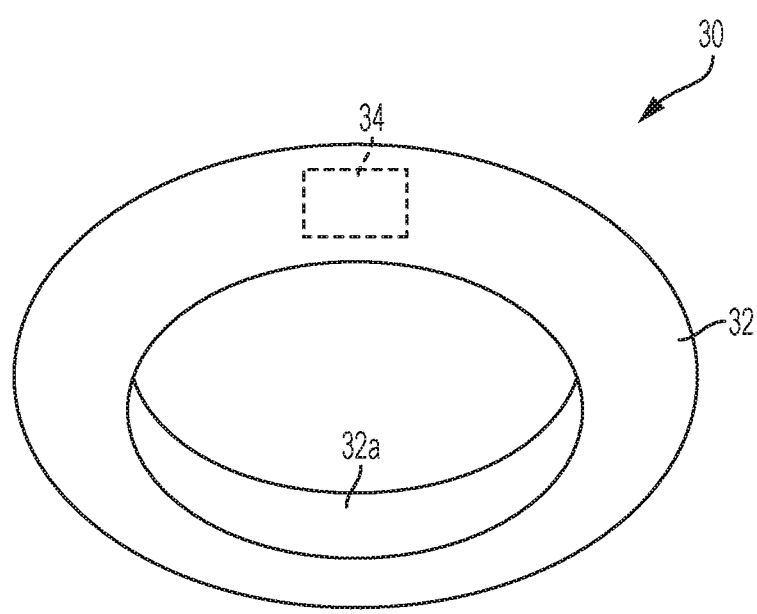
FIG. 4A is a perspective view of the wrist band of FIG. 2.
Figure 4B:
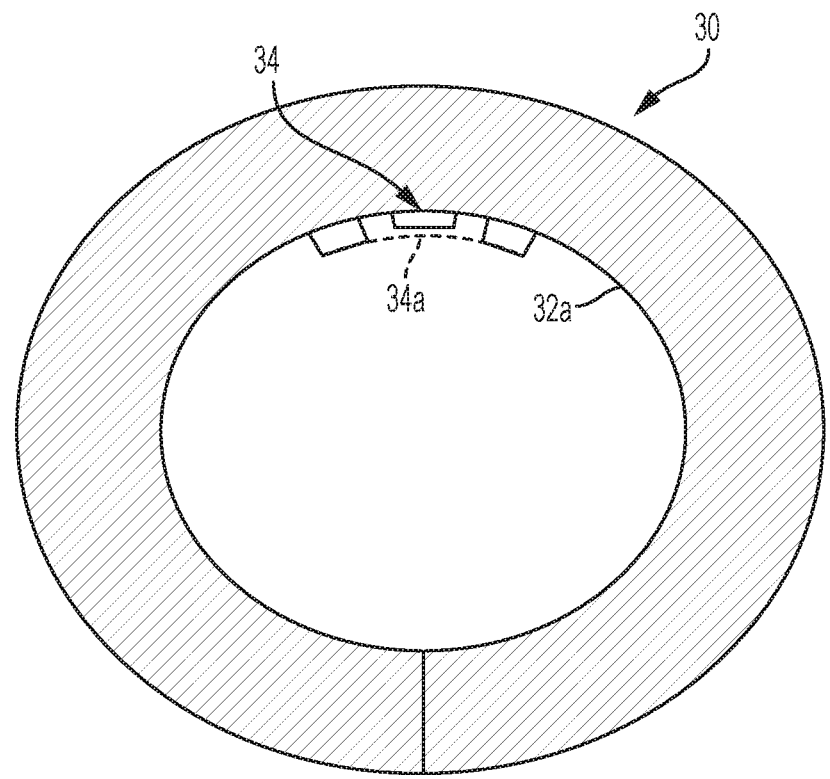
FIG. 4B is a cross sectional view of the wrist band of FIG. 4A illustrating a sensor module on an inside surface of the wrist band.

FIGS. 3 and 4A-4B illustrate a monitoring apparatus 30 in the form of a sensor band 32 configured to be secured to an appendage (e.g., an arm, wrist, hand, finger, toe, leg, foot, neck, etc.) of a subject. The band 32 includes a sensor module 34 on or extending from the inside surface 32a of the band 32. The sensor module 34 is configured to detect and/or measure physiological information from the subject and includes a sensor region 34a that may be contoured to contact the skin of a subject wearing the apparatus 30. For example, the sensor region 34a may comprise a photoplethysmography (PPG), bioimpedance sensor, ballistogram sensor, auscultatory sensor, thermal sensor, or the like.

The sensor modules 24, 34 for the illustrated monitoring devices 20, 30 of FIGS. 1, 2, 3 and 4A-4B are configured to detect and/or measure physiological information from a subject wearing the monitoring devices 20, 30. In some embodiments, the sensor modules 24, 34 may be configured to detect and/or measure one or more environmental conditions in a vicinity of the subject wearing the monitoring devices 20, 30.

A sensor module 24, 34 utilized in accordance with embodiments of the present invention may be an optical sensor module that includes at least one optical emitter and at least one optical detector, in a PPG sensor configuration, reflection-mode and/or transmission-mode. Exemplary optical emitters include, but are not limited to light-emitting diodes (LEDs), laser diodes (LDs), compact incandescent bulbs, organic LEDs (OLEDs), micro-plasma emitters, IR blackbody sources, or the like. Exemplary optical detectors include, but are not limited to, photodiodes, photodetectors, solar cells, CCD (charge-coupled device) cameras, photomultipliers, avalanche photodiodes, CMOS-imaging circuits, or the like. In addition, a sensor module may include various types of sensors including and/or in addition to optical sensors. For example, a sensor module may include one or more inertial sensors (e.g., an accelerometer, optical sensor, blocked-channel sensor, piezoelectric sensor, vibration sensor, photoreflector sensor, pressure sensor, etc.) for detecting changes in motion, one or more thermal sensors (e.g., a thermopile, thermistor, resistor, etc.) for measuring temperature of a part of the body, one or more electrical sensors for measuring changes in electrical conduction, one or more skin perspiration or humidity sensors, and/or one or more acoustical sensors.

Figure 5:
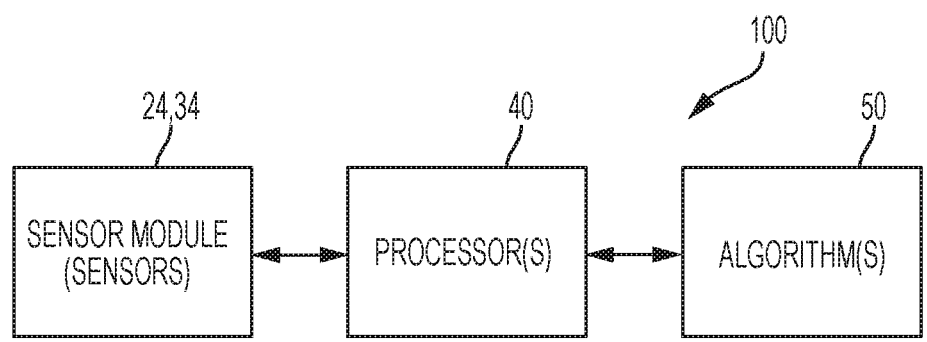
FIG. 5 is a block diagram of a system for enhancing the biometric performance of a person via musical audio, according to some embodiments of the present invention.

Referring to FIG. 5, a system 100 for enhancing the biometric performance of a person via musical audio, according to some embodiments of the present invention, is illustrated. The system 100 includes at least one processor 40 that is coupled to the sensor(s) of a sensor module 24, 34 and that is configured to receive and analyze signals produced by the sensor(s). The at least one processor 40 utilizes one or more algorithms 50 for enhancing the biometric performance of a person and/or modulating one or more biometric parameters via musical audio, as will be described below.

Figure 6:
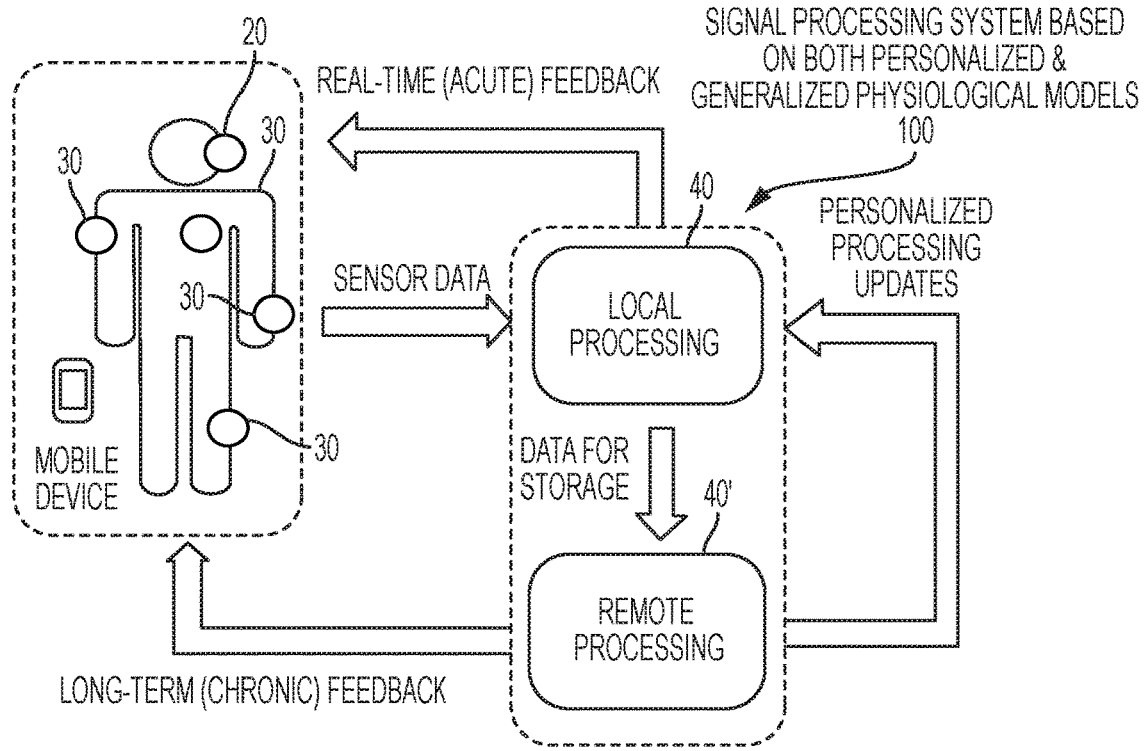
FIG. 6 is a block diagram of a system for enhancing the biometric performance of a person via musical audio using both acute and chronic feedback, according to some embodiments of the present invention.

FIG. 6 illustrates a system 100 for enhancing the biometric performance of a person via musical audio using both acute and chronic feedback, according to some embodiments of the present invention. The system 100 includes one or more monitoring devices 20, 30 configured to measure physiological information from the person wearing the devices 20, 30, such as heart rate, breathing rate, etc. One or more local processors 40 are configured to receive data from the sensors associated with the monitoring devices 20, 30 and to provide real-time (also referred to as "acute") feedback to the person based upon both personalized and generalized physiological models. In addition, the system 100 includes one or more remote processors 40' that are configured to process stored data from the devices 20, 30 and provide long-term (also referred to as "chronic") feedback to the person.

Additionally, a feedback loop is provided to update algorithms for personalized processing, based on long-term trends observed over time. For example, the remote processor 40' (such as a cloud processor) may process sets of acquired sensor data to determine that someone is at risk of a cardiac condition (such as arrhythmia, atrial fibrillation, a heart attack, stroke, and the like). In such case, feedback may be sent to at least one local processor 40 to update processing sources and to focus those processing resources on monitoring for the cardiac condition of interest. For example, the sampling frequency or polling of a sensor may be increased or an unpowered or sleeping sensor may be turned on or awakened.

Figure 7:
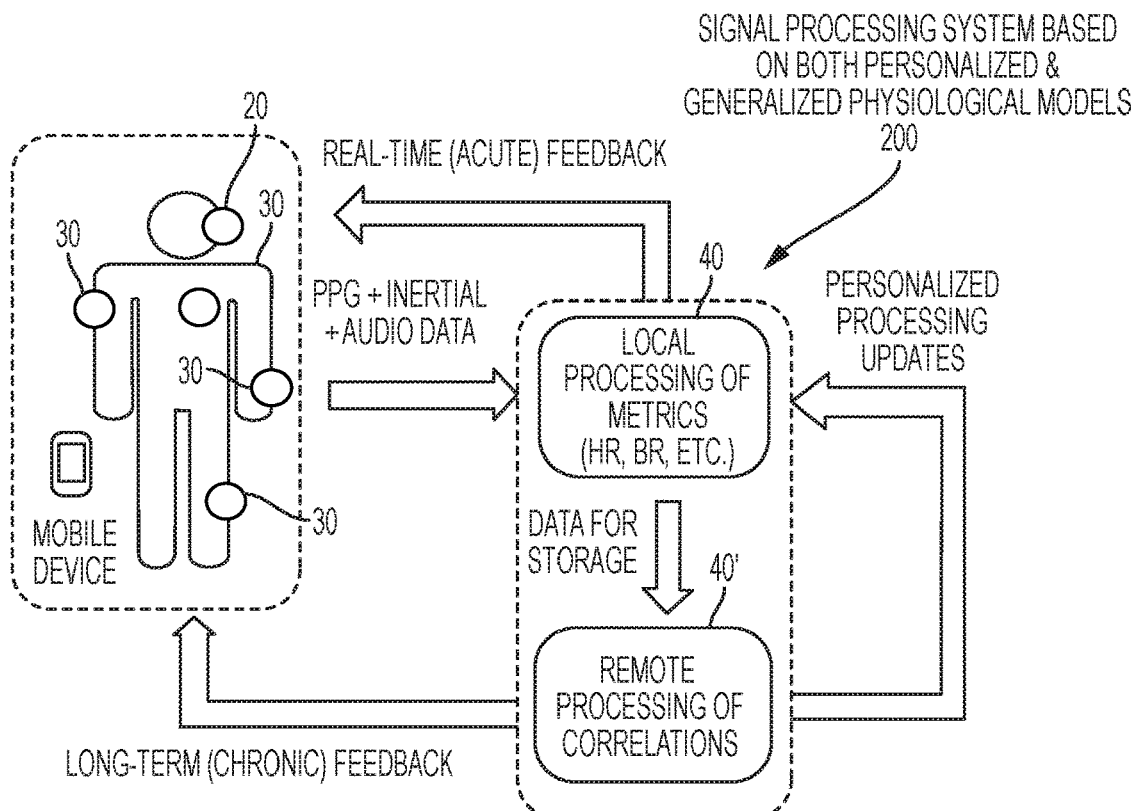
FIG. 7 is a block diagram of a system for enhancing the biometric performance of a person via musical audio using both acute and chronic feedback and wherein the sensor data includes PPG data, inertial data and audio data, according to some embodiments of the present invention.

FIG. 7 illustrates a specific embodiment of the system 100 of FIG. 6, namely a system 200 for enhancing the biometric performance of a person via musical audio using both acute and chronic feedback and wherein the sensor data includes PPG data, inertial data and audio data, according to some embodiments of the present invention. The system 200 includes one or more monitoring devices 20, 30 configured to measure PPG data, inertial data, and audio data. The audio data is from musical audio played to the person wearing monitoring device 20 (e.g., an earbud). One or more local processors 40 are configured to receive the PPG data, inertial data and audio data from the sensors associated with the monitoring devices and provide real-time (acute) feedback to the person based upon both personalized and generalized physiological models. In addition, the system 100 includes one or more remote processors 40' that are configured to process stored data from the devices 20, 30 and provide long-term (chronic) feedback to the person.

Figure 8:
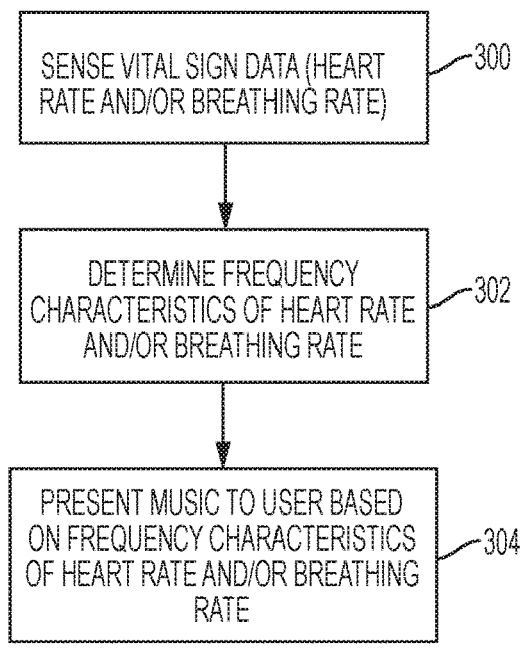
FIGS. 8-10 are flowcharts of operations for enhancing the biometric performance of a person via musical audio, according to some embodiments of the present invention.

Referring to FIG. 8, a method of controlling a biometric parameter of a person includes sensing vital sign data, such as, in this particular example, heart rate and/or breathing rate, via one or more monitoring devices 20, 30 (Block 300) and determining frequency characteristics of the heart rate and/or breathing rate (Block 302). Musical audio is then selected and presented to the person (e.g., via an audio earbud 20) based on the frequency characteristics of the person's heart rate and/or breathing rate (Block 304). By varying the tempo or other characteristic(s) of the musical audio, the person's breathing rate and/or heart rate can be modulated.

However, it is to be understood that characteristics of a photoplethysmogram, other than heartbeat or respiration rate frequency, also may be employed in embodiments of the present invention. For example, the amplitude, ramp rate, decay rate, shape, etc. of a PPG waveform may be characterized by a processor and then music may be presented to the user based on at least one of these characteristics. For example, if a processor determines that a person has a sharp rise-time (or fall-time) to his/her PPG waveform, the music may be modified such that every up-beat (or down beat) is accentuated or sped-up in time in order to resonate or correlate with that of the PPG waveform. Similarly, the tempo or amplitude of the music may be modified with the ramp-rate or decay-rate of a heart rate or breathing rate of the user. As another example, if the shape of a person's PPG waveform is "sawtooth" in nature, then the music may be modified such that the acoustical waveforms have a sawtooth characteristic. As yet another example, if a processor determines a person's heart rate and breathing rate are characterized by distinct frequencies or frequency bands, then the processor may modify the music such that harmonics of each frequency or frequency band are introduced into the playlist or are incorporated or alternated in a selected song.

As described earlier, PPG information may be processed into a variety of biometrics other than heart rate and breathing rate, for example, such as blood pressure, blood hydration level, blood analyte (blood oxygen, $CO_2$, CO, glucose, etc) level, R-R interval (RRi), heart rate variability (HRV) information, hemodynamic information, cardiac output, aerobic capacity ($VO_2$max), $VO_2$, metabolic rate, health status information, breathing volume (inhalation and exhalation volume) and the like. These biometrics may also comprise frequency characteristics that can be mapped to musical frequencies, and some embodiments of the present invention, such as those described with respect to FIG. 8 and FIG. 9, may be applied using these biometrics instead of, or in addition to, heart rate and breathing rate.

Figure 9:
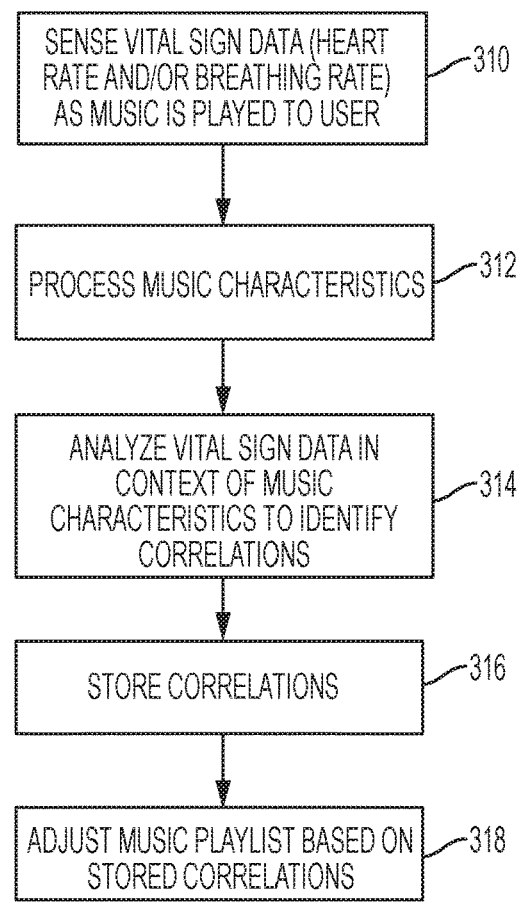

Referring to FIG. 9, a method of controlling a biometric parameter of a person includes sensing vital sign data, such as heart rate and breathing rate, via one or more monitoring devices 20, 30, as musical audio is played to the person, for example via an audio earbud 20 (Block 310). One or more characteristics of the music, such as tempo, pitch, frequency, rhythm, articulation, order, cadence, instrumentation characteristics, tone, voice characteristics, and the like, are processed (Block 312). The vital sign data from the person is then analyzed in context with the music characteristics to identify any correlations (Block 314) and these correlations are stored (Block 316). A music playlist may then be adjusted to play musical audio to the person based on one or more stored correlations between music and vital signs data (Block 318). As an example, a processor may determine that high voice pitch (or treble-rich music) is correlated with higher user heart rate, and the processor may then adjust the playlist to play high-voice-pitch music to increase heart rate of the user or to play low-voice-pitch music (or bass-rich music) to lower heart rate of the user.

Figure 10:
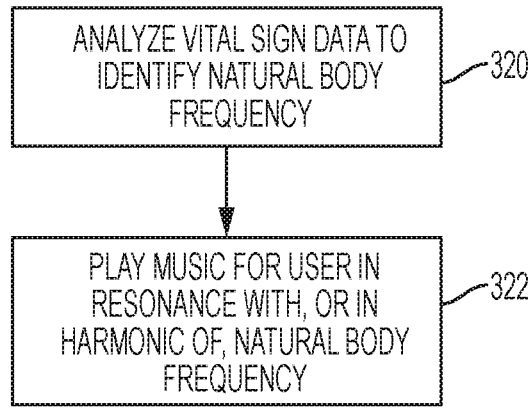

Referring to FIG. 10, a method of enhancing the biometric performance of a person via audio includes analyzing vital sign data (e.g., heart rate, breathing rate, etc.) from a person to identify natural body frequency (Block 320). Musical audio is then played to the person, for example via an audio earbud 20, in resonance with or in a harmonic of, the natural body frequency of the person (Block 322). For example, in one embodiment of this invention, both heart rate and respiration rate are determined by a processor, and the audio is selected to manipulate the respiration rate (as described below with respect to FIG. 11) such that the respiration rate and heart rate are always in resonance with each other (i.e., they share a fundamental frequency or the heart rate variability is highest).

Another method of enhancing the biometric performance of a person via musical audio, in accordance with embodiments of the present invention, may include analyzing vital sign data (e.g., heart rate, breathing rate, etc.) from a person as well as analyzing physical activity data (user cadence, speed, pace, gait, etc.) from the person and notifying the person when the cadence and vital sign are characterized by the same fundamental frequency. Additionally, the music playlist may be adjusted to this common frequency (or pitch) or the songs may be stretched or compressed in time to match this common frequency or to match with at least a harmonic of the fundamental frequency.

There may be physiological benefits to running at or exercising at a cadence that shares a fundamental frequency with one's heart rate and/or respiration rate. For example, as with impedance matching for electrical circuits, the pumping mechanism of the cardiopulmonary system may require less work to generate sufficient blood flow when the exercising cadence resonates with the heart rate of the person. As such, notifying a person that his/her cadence and heart rate are not resonating (i.e. are not equal or do not share a common fundamental frequency) can enable the person to change cadence and minimize total energy expenditure for a given workload. Alternately, if the person wants to increase total energy expenditure for a given workload, then the person may want to exercise at a cadence that does not resonate with heart rate. Thus, notifying the user of resonance between at least one vital sign and at least one exercise cadence can help train the person to better exercise efficiency or to intentionally poorer exercise efficiency.

Figure 11:
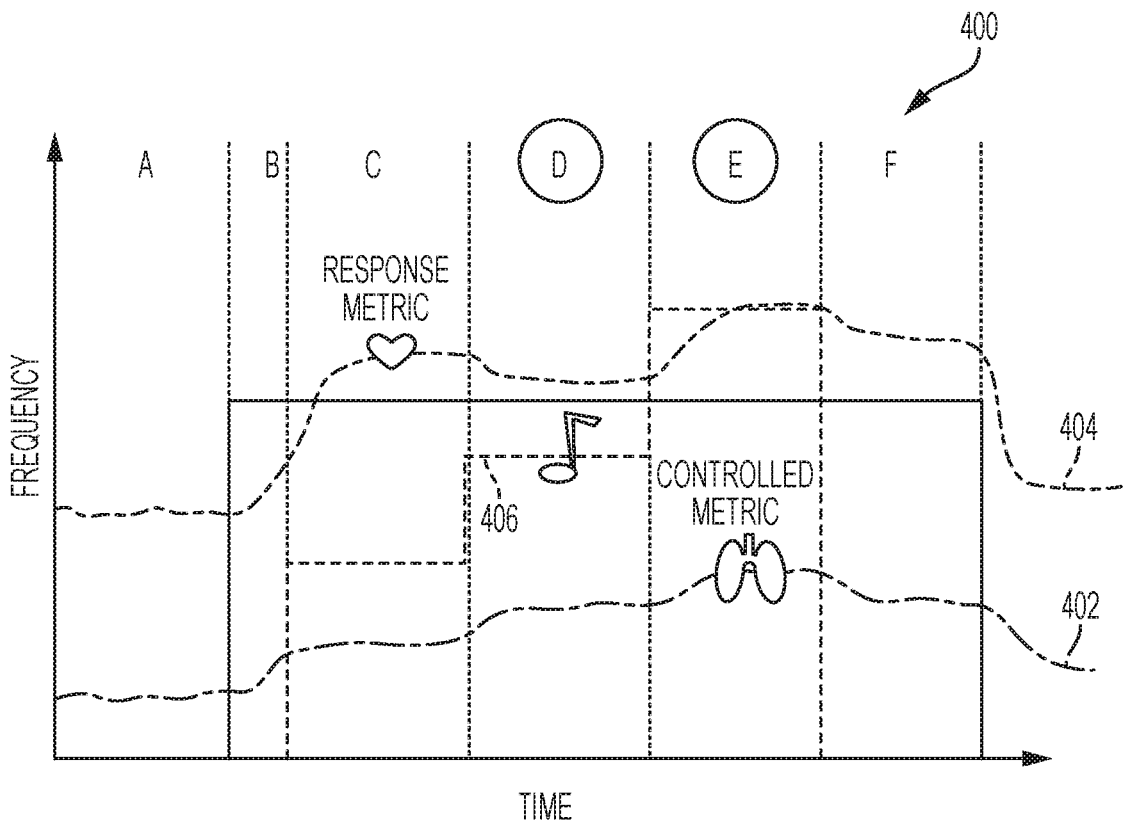
FIG. 11 is a plot illustrating a method of determining optimal breathing rate and music tempo for minimum or maximum cardiac exertion at a steady cadence, according to some embodiments of the present invention.

FIG. 11 is a plot 400 of a response metric 404 and controlled metric 402 over time that illustrates a method of determining optimal breathing rate and music tempo for minimum cardiac exertion at a steady cadence, according to some embodiments of the present invention. In FIG. 11, the controlled metric 402 is respiration rate and the response metric 404 is heart rate. Applicant has discovered that a person's respiration rate may subconsciously track with a harmonic of the tempo of a given musical audio heard by the person. In such case, the person's respiration rate may be controlled by the music, and heart rate may respond to the respiration rate. As such, an optimal controlled metric associated with an optimal response metric, for a given workload (or more generally, "activity state"), can be learned.

Initially, a person listens to musical audio while exercising at a constant cadence. The musical audio changes tempo 406 while the user is exercising, and the person's breathing rate 402 may naturally lock-in to a harmonic of the musical audio tempo 406. In turn, the user's heart rate may fluctuate with breathing rate, during exercise at a constant work-load by the user. Thus, the ideal breathing rate 402 (and associated musical audio tempo) for minimal cardiac exertion/ workload (i.e., minimum heart rate (HR) at a given workload) may be identified as that in time period D, which is associated with the minimum HR 404 during a steady cadence (i.e., minimal energy expenditure for a given workload or minimal heart rate for a given workload). However, in the case where weight-loss is desired, the opposite goal may be desired. Namely, the ideal breathing rate 402 (and associated music temp 406) for maximal energy expenditure/workload is identified as that of time period E, which is associated with the maximum cardiac exertion/energy expenditure (i.e., maximum HR at a given workload).

Figure 12:
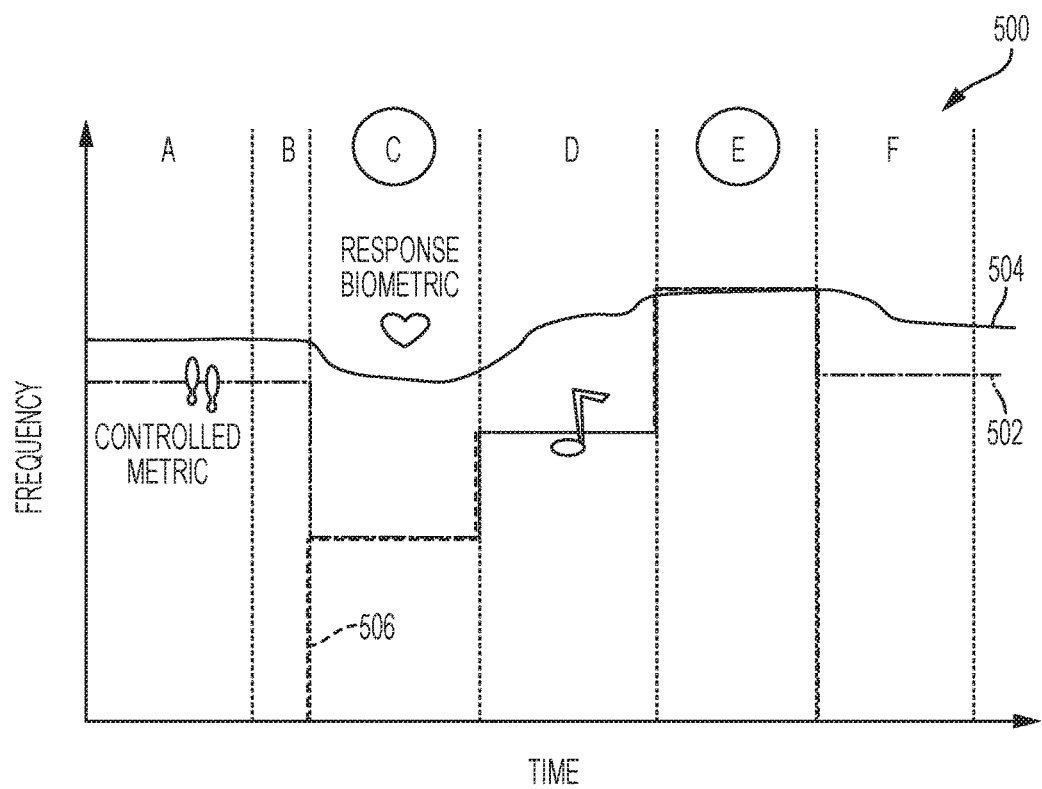
FIG. 12 is a plot illustrating a method of determining optimal cadence and music tempo for minimum or maximum cardiac exertion at a steady speed, according to some embodiments of the present invention.

FIG. 12 is a plot 500 of a response metric 504 and controlled metric 502 over time that illustrates a method of determining optimal cadence and music tempo for minimum cardiac exertion at a steady speed, according to some embodiments of the present invention. In FIG. 12, the controlled metric 502 is cadence, such as step rate, cycling cadence, exercise cadence, etc., and the response metric 504 is heart rate (HR). Applicant has discovered that a person's cadence 502 may subconsciously track with a harmonic of the tempo of a given musical audio heard by the person. In such case, the person's cadence is controlled by the music, and heart rate responds to this cadence. As such, an optimal controlled metric associated with an optimal response metric, for a given activity state, such as workload, can be learned.

Initially, a person listens to musical audio while exercising at a steady speed. The musical audio changes tempo 506 while the user is exercising, and the person's cadence rate 502 naturally locks-in to a harmonic of the musical audio tempo 506. The ideal cadence rate 502, and associated musical audio tempo, for minimal cardiac exertion is identified as that associated with the minimum HR 504 during a steady cadence as shown in time period C. However, in the case where weight-loss is desired, the ideal cadence rate 502, and associated musical audio tempo 506 for maximal energy expenditure at the same running speed is identified as that associated with the maximum cardiac exertion (maximum HR 504), as shown in time period E.

Figure 13:
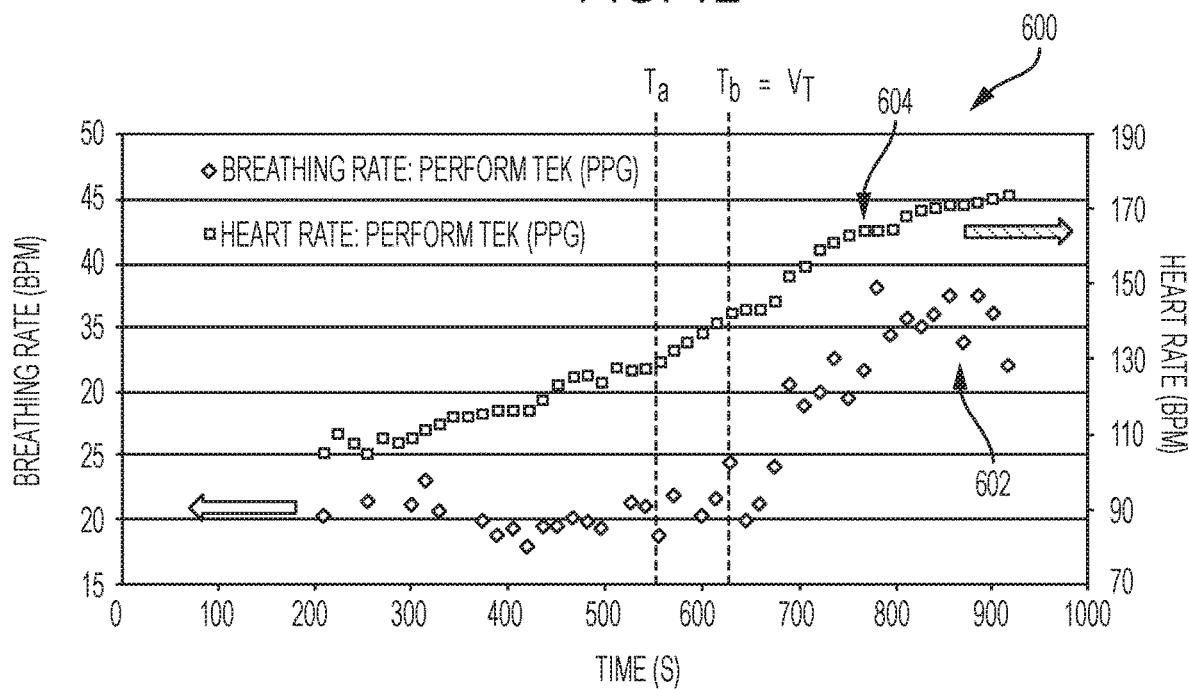
FIG. 13 is a plot of breathing rate and heart rate data collected over a period of time for a person and from which the ventilator threshold ($V_T$) can be estimated, according to some embodiments of the present invention.
Figure 14:
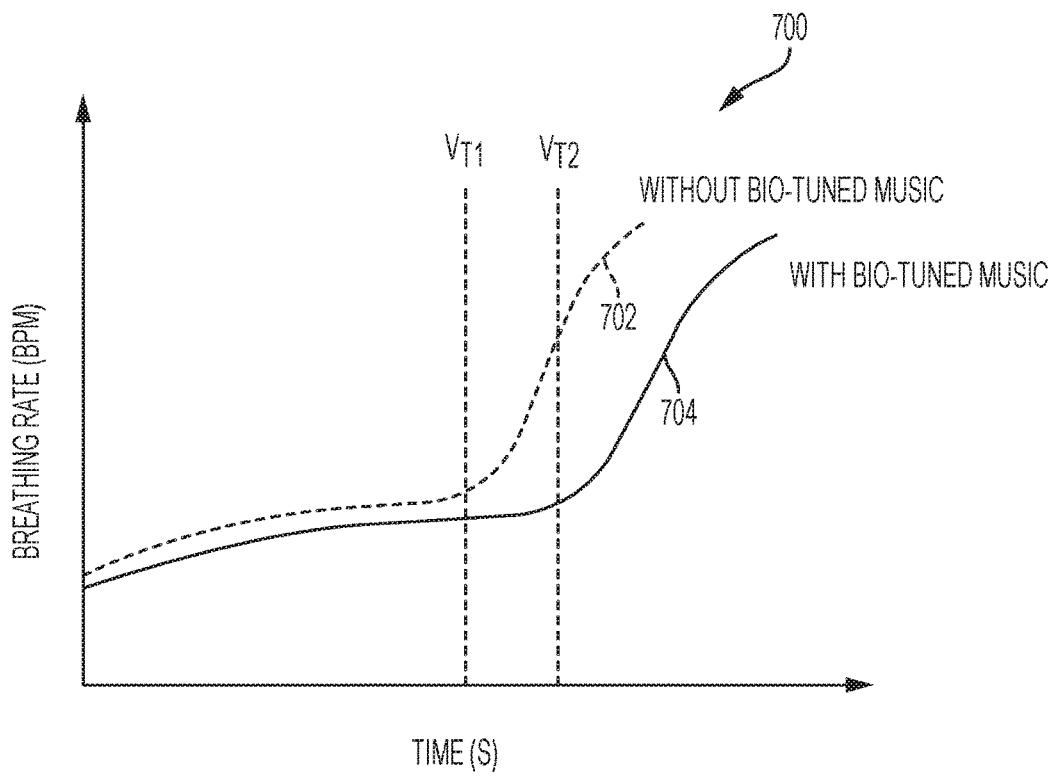
FIG. 14 is a plot of breathing rate over time for a person and illustrating the manipulation of $V_T$ via musical audio, according some embodiments of the present invention.

In addition to heart rate (HR) and breathing rate (BR), other body metrics that may be modulated by musical audio and monitored to optimize the use of music with respect to exercise include, but are not limited to, body temperature, blood pressure, cardiac output, RRi, and ventilatory threshold ($V_T$). Body temperature can be measured via a body temperature sensor, or estimated via monitoring HR and/or BR at a constant workload. Using musical audio to manipulate BR to reduce HR for a given speed can be used to push out $V_T$ in time (pushing it out to a higher heart rate), thereby pushing out the transition between aerobic and anaerobic exercise. This is illustrated in FIGS. 13 and 14 and described below. RRi may be measured by identifying heart beat peaks or frequencies in a PPG waveform (using time-domain or frequency domain analysis) and then reporting time periods between each heart beat. The user's time-between-heart-beats may lock-in to the time-between-music-beats such that one's RRi may be controlled by the music beat.

FIG. 13 is a plot 600 of BR data 602 and HR data 604 collected over a period of time for a person and from which ventilatory threshold $V_T$ can be estimated, according to some embodiments of the present invention. Data was collected from a person wearing a monitoring device having PPG-based sensor technology during a $VO_2$max test. The person was wearing an audio earbud 20, but could have also been wearing a wrist band 30 (or armband, legband, ring, patch, etc.) containing a sensor module 24, 24. The monitoring device 20 sensed photoplethysmograms (via a PPG sensor) and motion (via a motion sensor) and processed the signals (via a processor) to attenuate motion noise and generate metrics for HR, BR, distance, speed, pace, cadence, $VO_2$ (oxygen volume consumption), blood pressure, RRi (R-R interval), and other biometrics.

By definition, ventilatory threshold ($V_T$) is the point at which ventilation begins increasing at a faster rate than $VO_2$. From the time-dependent HR and $V_T$ data, one can estimate the ventilatory threshold ($V_T$) as the point at which BR increases rapidly (such as when the slope of BR vs. time increases). Greater confidence in the $V_T$ estimation can be derived by also noting the presence of a HR inflection ($T_a$) a few minutes ahead of $V_T$ ($T_b$).

Additionally, a person's workload may also be factored into an algorithm for determining $V_T$. As a specific example, if a wearable device 20, 30 includes a motion sensor, such as an accelerometer, an inflection in the motion sensor signal (such as the intensity or cadence, for example) may trigger the algorithm to begin looking for $V_T$ or may be factored into an algorithm for estimating $V_T$. Generally speaking, $V_T$ will only be observed at a workload high enough to sufficiently tax aerobic capacity, and thus knowledge of a person's workload and aerobic capacity (such as $VO_2$max) may be used to determine regions in time wherein the person may experience $V_T$.

$V_T$ is an important biometric assessment because it can indicate the transition of a body from aerobic to anaerobic exercise, and can also be associated with lactic threshold. Additionally, before $V_T$, an estimation of energy expenditure (related to $VO_2$) can be a linear relationship factoring HR as the variable: EE=k*$VO_2$=m*HR+b, where EE=energy expenditure, k=constant, m=slope, HR=heart rate, and b=intercept. After $V_T$ is reached, since HR rate may not be changing (and indeed HR may be saturating) in time, a different relationship for energy expenditure may be required. Namely, the algorithm for energy expenditure may branch at $V_T$, such that two separate algorithms are employed before and after $V_T$ is reached. For example, before $V_T$, the aforementioned EE=m*HR+b may be employed, and after $V_T$, an alternative relationship between EE and HR may be employed. Alternatively, after $V_T$ is reached, a relationship between EE and BR may be employed, where heart rate is not factored into the equation. For example, EE may increase linearly with increasing BR after $V_T$ is reached.

FIG. 14 is a plot of BR 702 (without bio-tuned music), 704 (with bio-tuned music) over time for a person and illustrating the manipulation of $V_T$ via musical audio, according some embodiments of the present invention. Specifically, FIG. 14 illustrates how "bio-tuning musical audio" can push-out $V_T$. For example, once an optimal musical tempo is identified for minimizing energy expenditure (EE), $VO_2$, or HR for a given workload, the bio-tuned musical audio can be used to shift-out $V_T$ during a maximal exercise, such as for a $VO_2$max test or for intense training. Thus, the person may be better able to endure greater workloads without reaching exhaustion as quickly.

Figure 15:
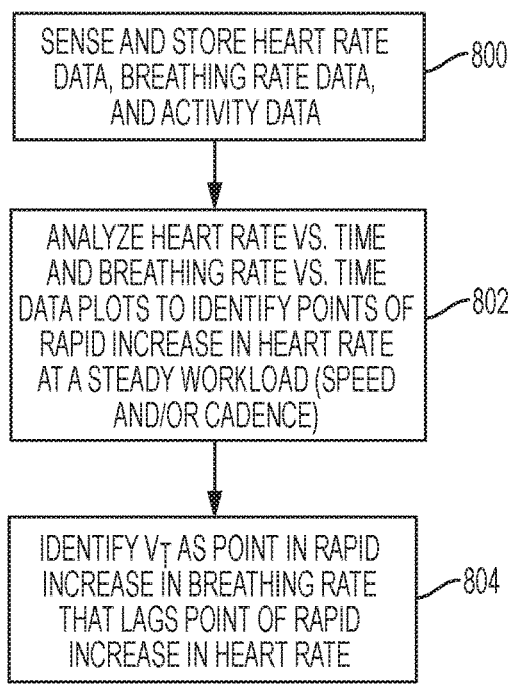
FIGS. 15-17 are flowcharts of operations for enhancing the biometric performance of a person via audio, according to some embodiments of the present invention.

Referring to FIG. 15, a method of determining $V_T$ in a person wearing a monitoring device 20, 30 having a PPG sensor and motion sensor, according to some embodiments of the present invention, is illustrated. HR, BR and activity data (motion data) is sensed via a monitoring device 20, 30 and stored (Block 800). Data plots of HR vs. time and BR vs. time are analyzed to identify points of rapid increase in HR at a steady workload (e.g., steady speed and/or cadence) (Block 802). $V_T$ is then identified as a point in rapid increase in BR that lags a point of rapid increase in HR (Block 804).

It should be noted that a variety of methods may be employed to determine the timing that $V_T$ is reached. For example, an alternate method of determining the time that $V_T$ is reached may be to analyze at least a few seconds of data to see when the slope of BR vs. HR changes substantially. As can be observed from FIG. 13, the BR does not change substantially with increasing HR until $V_T$ is reached, at which point the change in BR vs. HR increases substantially (i.e., the slope of BR vs. HR increases substantially). By "substantially", this may mean a change in slope of 5% or higher over a period of sixty (60) or more seconds.

Figure 16:
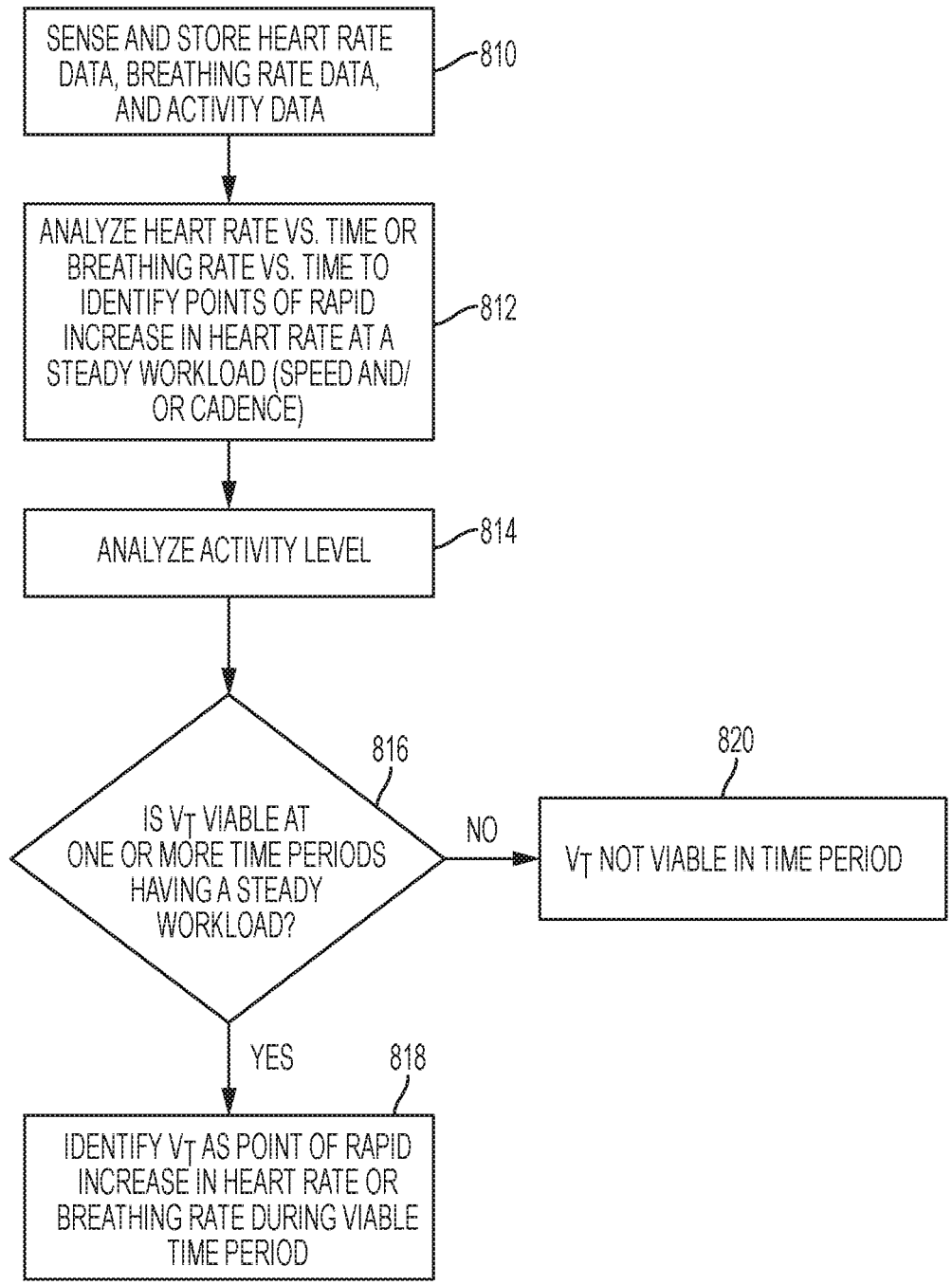

Referring to FIG. 16, another method of determining $V_T$ in a person wearing a monitoring device 20, 30 having a PPG sensor and motion sensor, according to some embodiments of the present invention, is illustrated. HR and/or BR data and activity data (motion data) is sensed via a monitoring device 20, 30 and stored (Block 810). Data plots of HR vs. time and/or BR vs. time are analyzed to identify points of rapid increase in HR and/or BR at a steady workload (e.g., steady speed and/or cadence) (Block 812).

Activity level of the person is analyzed (Block 814) and a determination is made if $V_T$ is viable at one or more time periods where the person has a steady workload (Block 816). For example, physiological models (such as theoretical or experiential models) may include relationships between a given workload and whether $V_T$ can be reached at those workloads. These models may also incorporate static characteristics about a person, such as age, height, and gender, as well as quasi-static characteristics, such as weight and cardiac efficiency. Using cadence or speed as a proxy for workload, at least one model can be used to determine whether $V_T$ is viable. In some embodiments, the model may also include information about heart rate, such that $V_T$ is viable at only certain workloads and certain heart rates. In any case, if a processor determines that $V_T$ is viable, $V_T$ is identified as a point of rapid increase in HR or BR during the viable time period (Block 818). If the answer is no, $V_T$ is not viable in the time period (Block 820). The method of FIG. 16 can be a "looped" process such that it is continually analyzed in time to mark periods of $V_T$ being viable or not viable.

Figure 17:
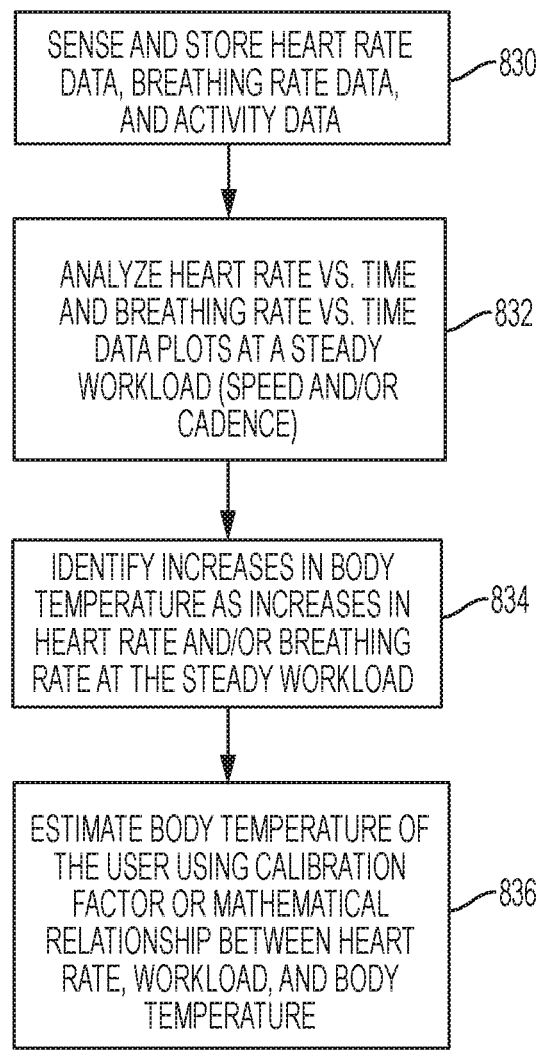

Referring to FIG. 17, a method of determining body temperature of a person wearing a monitoring device 20, 30 having a PPG sensor and motion sensor, according to some embodiments of the present invention, is illustrated. HR, BR and activity data (motion data) is sensed via a monitoring device 20, 30 and stored (Block 830). Data plots of HR vs. time, HRV vs. time, and/or BR vs. time are analyzed to identify points of rapid increase in HR, HRV, and/or BR at a steady workload (e.g., steady speed and/or cadence) (Block 832). Increases in body temperature are identified as significant changes in HR, HRV and/or BR at the steady workload (Block 834).

In particular, HR and BR may significantly increase with increasing body temperature and HRV may have spectral (frequency-domain) components with spectral coefficients that either increase or decrease with body temperature. Since HR can be measured using data from a PPG sensor, the body temperature of the person can then be estimated using a calibration factor or mathematical relationship between the measured HR and body temperature for a given workload (Block 836).

Body temperature may also be estimated using a calibration factor or mathematical relationship between BR and temperature for a given workload or a mathematical relationship between HRV and body temperature for a given workload. In this particular example, it may be beneficial to estimate workload using data from the inertial sensor(s) in the wearable device worn by the user. A variety of methods for estimating workload using wearable inertial sensors are well known to those skilled in the art.

Figure 18:
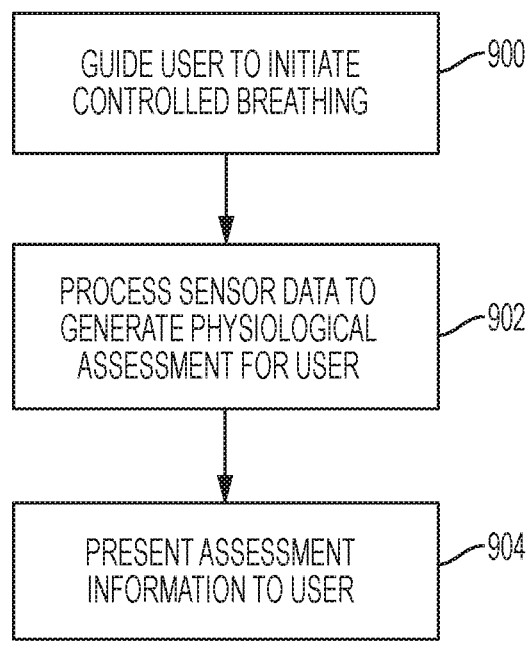
FIGS. 18-19 are flowcharts of operations for guiding a subject to control breathing such that a physiological assessment may be generated for the subject based on biometric sensor data collected during the guided controlled breathing, according to some embodiments of the present invention.

In some embodiments, the present invention may be used to help guide a user to controlled breathing, such that a physiological assessment may be generated for the user based on biometric sensor data collected during the guided controlled breathing, as shown in FIG. 18. In this method, a user wearing a biometric sensor, such as the wearable sensors described in FIGS. 1-5, or a user utilizing a sensor system, such as that presented in FIGS. 6-7, may be audibly, and perhaps also visually, guided into a state of controlled breathing (Block 900). As a specific example, an animated character may be presented on a view-screen to demonstrate inhaling and exhaling, such that the user adapts to the breathing rate of the character on the view screen. Alternatively or additionally, the user may be presented with audible instructions for inhaling and exhaling, such as being presented with breathing sounds for inhaling and exhaling or with music that follows inhalation and exhalation, at the frequency of the targeted breathing rate or breathing volume. The audio and visual feedback may be provided by the wearable device itself or another part of the system of FIG. 6 or FIG. 7, such as a phone, computer, or the like.

As the user is being guided, a processor may process biometric sensor data to generate a physiological assessment for the user (Block 902). Nonlimiting examples of such physiological assessments are presented in FIGS. 22-24. But more generally, such physiological assessments may comprise an assessment of one's: health status, physical fitness, stress status (physical and/or mental), a biometric (such as blood pressure, cardiac functioning, blood oxygenation, or the like), or the like. The assessment(s) may then be presented audibly, and perhaps also visually, to the user (Block 904).

A key benefit of generating a physiological assessment during controlled breathing is that recurring measurements of the physiological assessment may be more useful for long-term trending, as one's metabolic activity may be more normalized for each measurement. As a specific example, generating a daily data point for a physiological assessment, such as blood pressure, during the same time of day over the course of several months can be useful for monitoring significant deviations in one's average blood pressure to decide if a medical intervention is warranted. In this case, one assumption is that measuring at the same time of day may help reduce artifacts associated with one's physical activity or metabolic activity, as one's physical activity and metabolic activity may be generally consistent at the same time of day. However, one's activity level and metabolic level may not always be the same during the same time of day, and thus guiding a user to controlled breathing may help normalize the user's physical activity and/or metabolic activity during regular measurements of blood pressure, such that long-term trending of blood pressure is more consistent, yielding more accurate determinations as to whether or not a medical intervention is warranted in response to the detection of significant changes in blood pressure compared with average blood pressure readings.

In some embodiments, the method of FIG. 18 may be incorporated into a game having a goal. In this way, generating an important physiological assessment can also be entertaining. For example, a gaming character may be able to unlock and utilize certain skills, weapons, or powers once a state of controlled breathing or relaxation is detected. Once the gaming goals are achieved, a physiological assessment may be presented to the user.

In some embodiments, the method of FIG. 18 may be utilized to generate a physiological assessment of one's stress sensitivity. For example, a physiological assessment may be generated before and after one has reached controlled breathing. The processor may then compare the before and after readings of this physiological assessment to determine if these readings are substantially different for uncontrolled vs. controlled breathing. The determination of a substantial difference may yield an assessment regarding one's stress sensitivity for presentation to the user, and this assessment may have therapeutic implications. As a specific example, if one's blood pressure readings are determined to be satisfactory (i.e., "normal") for controlled breathing and poor (i.e., "too low" or "too high") for uncontrolled breathing, one's stress sensitivity may be determined to be "high". A high stress sensitivity may then be presented to the user (or the user's trainer, physician, caretaker, or the like), implying that stress-reduction therapy may be effective in helping the user maintain a satisfactory blood pressure. In contrast, if one's before and after readings are found to be essentially identical, one's stress sensitivity assessment may be determined to be "low", such that stress-reduction therapy may not be particularly useful for the user. Some individuals may be more likely to benefit physiologically from controlled breathing and similar stress-reduction methodologies than others. For individuals who are stress-sensitive, non-pharmacological therapies may be more desirable for improving health than drugs, which may be associated with undesired side-effects. Thus, a key importance of this invention is that enabling a physiological assessment before and after controlled breathing provides a measurable way of determining whether stress-reduction methodologies would be useful for improving an individual's health.

Figure 19:
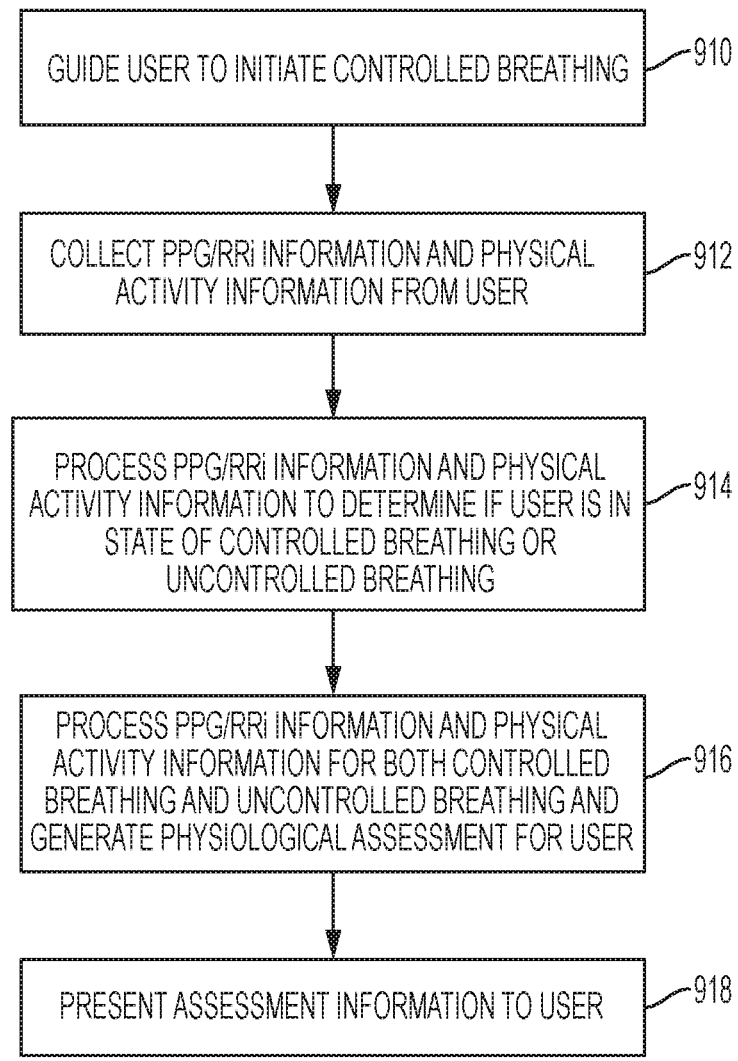

A specific embodiment of the method of FIG. 18 is presented in FIG. 19. For example, FIG. 19 illustrates a method of generating assessments by guided controlled breathing while monitoring RRi and physical activity via a wearable sensor capable of measuring both RRi information and physical activity information. In this method, the user may be wearing a wearable sensor device (e.g., monitoring device 20, 30) comprising a PPG sensor or another sensor for measuring RRi (i.e., an ECG sensor, an auscultatory sensor, a piezoelectric sensor, a ballistogram sensor, a bioimpedance sensor, or the like) and physical activity information, wherein the device is in communication with a view-screen and/or audio device such that the user may be guided towards controlled breathing visually and/or audibly, as described above (Block 910). If the user is wearing a PPG device that also comprises an inertial sensor, this collected sensor information (Block 912) may be processed into RRi information and/or breathing rate information as described in FIG. 20, by using a variable filter as described in U.S. Patent Application Publication No. 2014/0114147, which is incorporated herein by reference in its entirety, or by using other methods.

Regardless of the signal processing methodology used to generate RRi, the RRi information may then be processed by a processor to determine if the user is in a state of controlled breathing or a state of uncontrolled breathing (Block 914). One method for determining controlled breathing vs. uncontrolled breathing is explained via FIG. 20 and FIG. 21, but other methods may be used. Once the RRi data from periods of controlled and uncontrolled breathing are collected, the data may be processed to generate a physiological assessment for the user, as described above (Block 916). The assessment(s) may then be presented to the user, or someone monitoring the user, visually and/or audibly (Block 918).

Figure 22A:
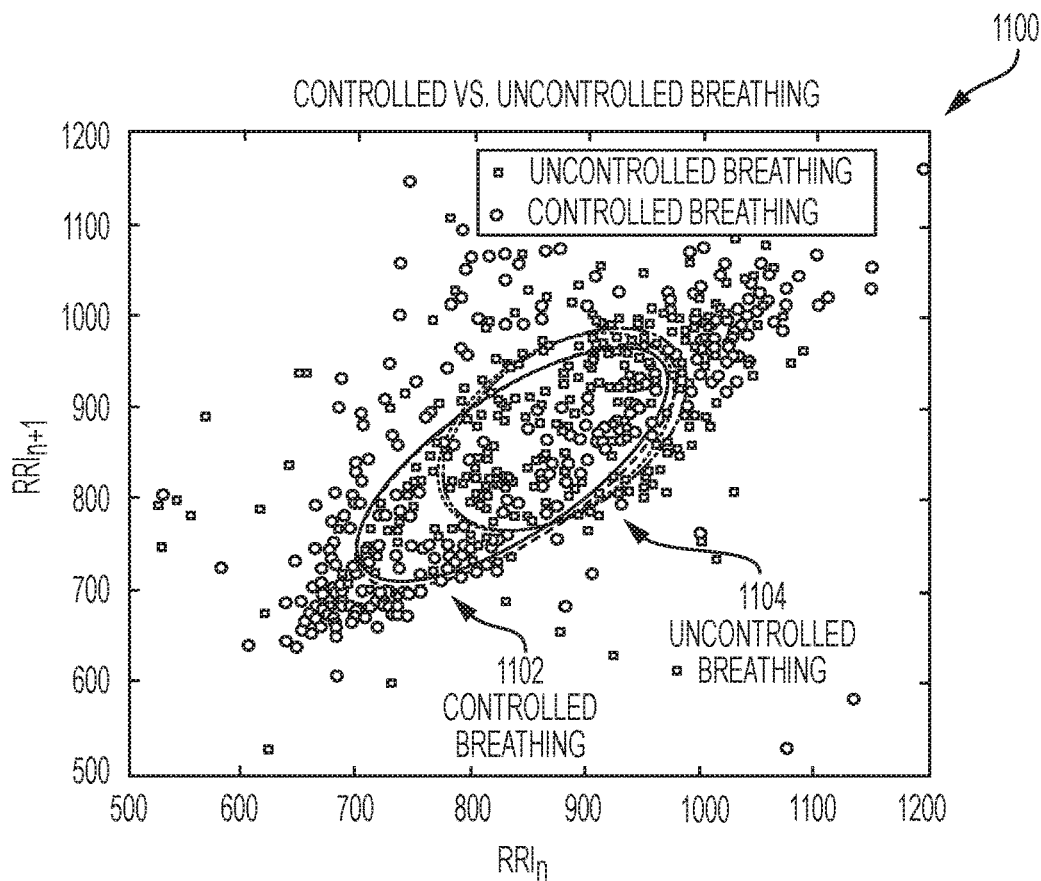
FIG. 22A is a Poincaré plot showing successive RR-intervals from FIG. 21 plotted against each other.
Figure 22B:
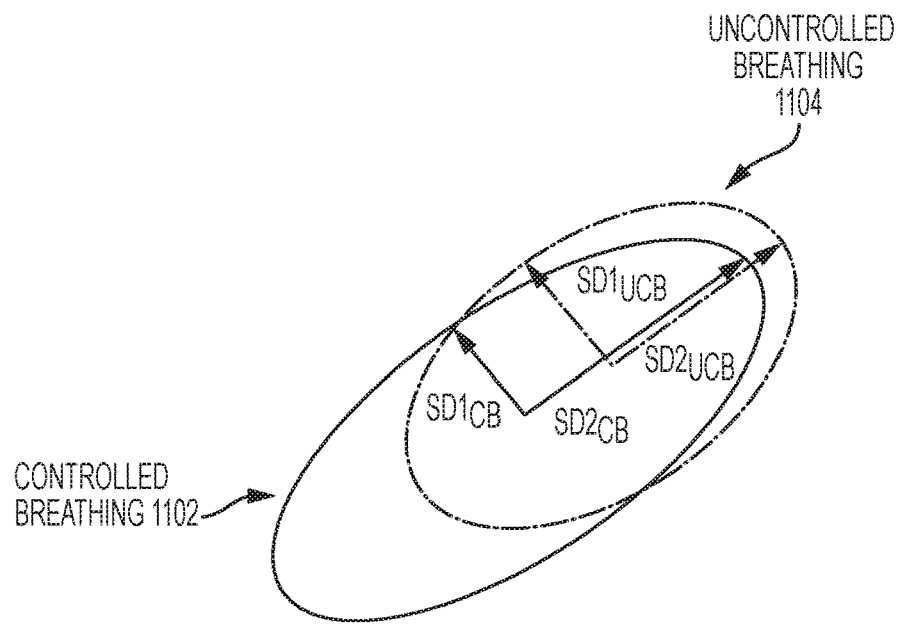
FIG. 22B illustrates ellipses that fit upon data points for controlled and uncontrolled breathing in FIG. 22A.
Figure 23:
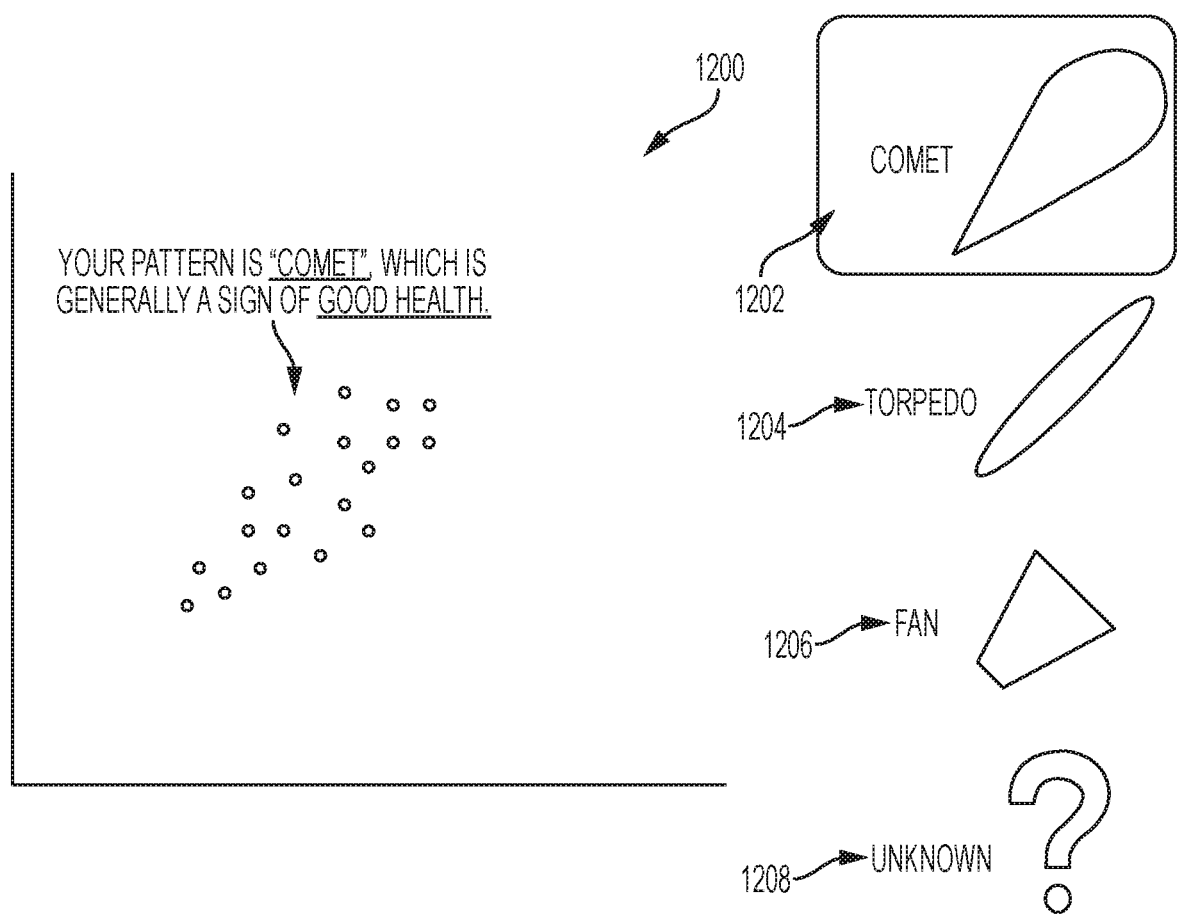
FIG. 23 illustrates a physiological assessment presentation, according to some embodiments of the present invention.

For example, FIGS. 22A-22B and FIG. 23 present particular examples of providing a health assessment with diagnostic value to an end user based on the method of FIG. 19.

Figure 20:
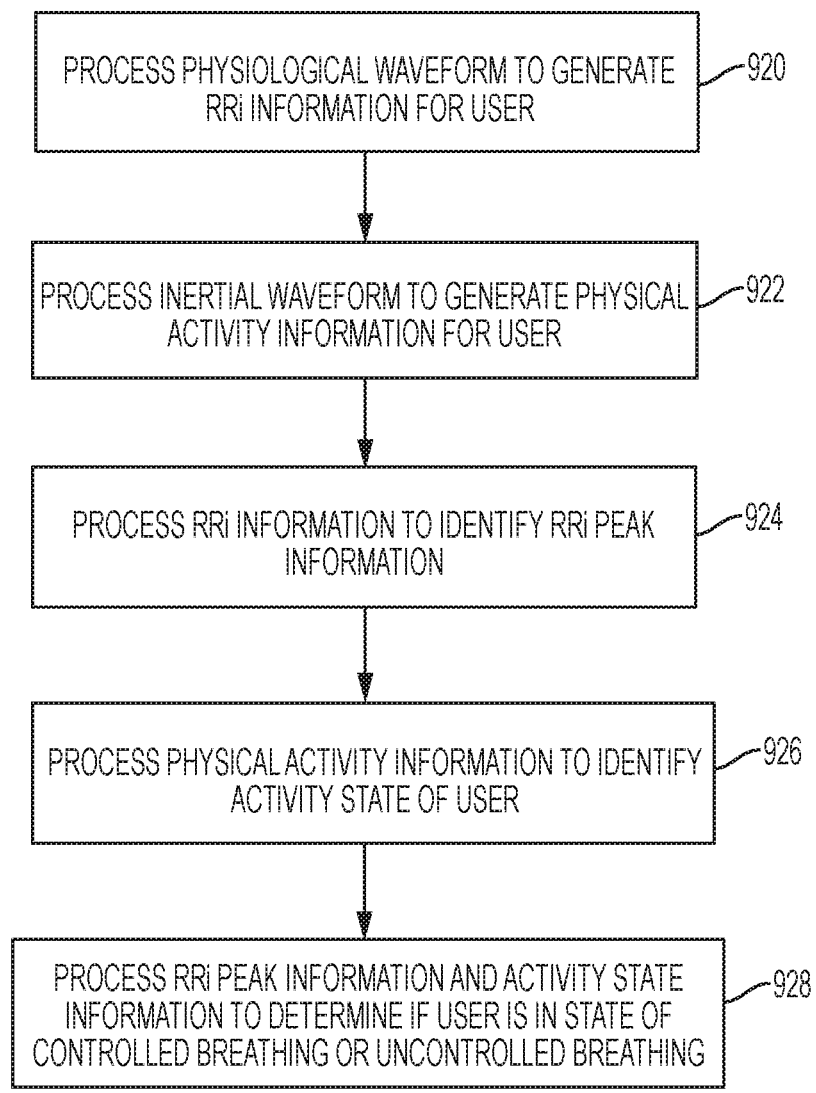
FIG. 20 is a flowchart of operations for determining if a subject is in a state of controlled breathing or uncontrolled breathing, according to some embodiments of the present invention.

A specific method of processing RRi and physical activity information to determine if the user is in a state of controlled breathing or uncontrolled breathing is presented in FIG. 20. As described earlier, this method can be used within the assessment generation method presented in FIG. 19. In this method, a physiological waveform (PPG, ECG, bioimpedance, auscultatory, or the like) is processed to generate RRi information (Block 920). Similarly, a physical activity waveform (accelerometry, gyroscopy, speedometry, and the like) is processed to generate physical activity information (cadence, speed, acceleration, position, exercise intensity, motion intensity, motion or rest duration, and the like) for the user (Block 922). The RRi information is then processed to identify peaks in the RRi-vs.-time (Block 924), and the physical activity information is processed to identify an activity state of the user (Block 926). The RRi peak information and activity state information can then be processed to determine if the user is (or is not) in a state of controlled breathing (Block 928). As a specific example, the RRi peaks during controlled breathing may have a period and frequency within a range that is characteristic of controlled breathing due to respiratory sinus arrhythmia and knowledge about the activity state of the user may be applied towards ascertaining if the person is at a state of relative "rest" (low activity) suitable for controlled breathing. This information may be processed together (Block 928) to assess whether a subject is truly in a state of controlled breathing.

Figure 21:
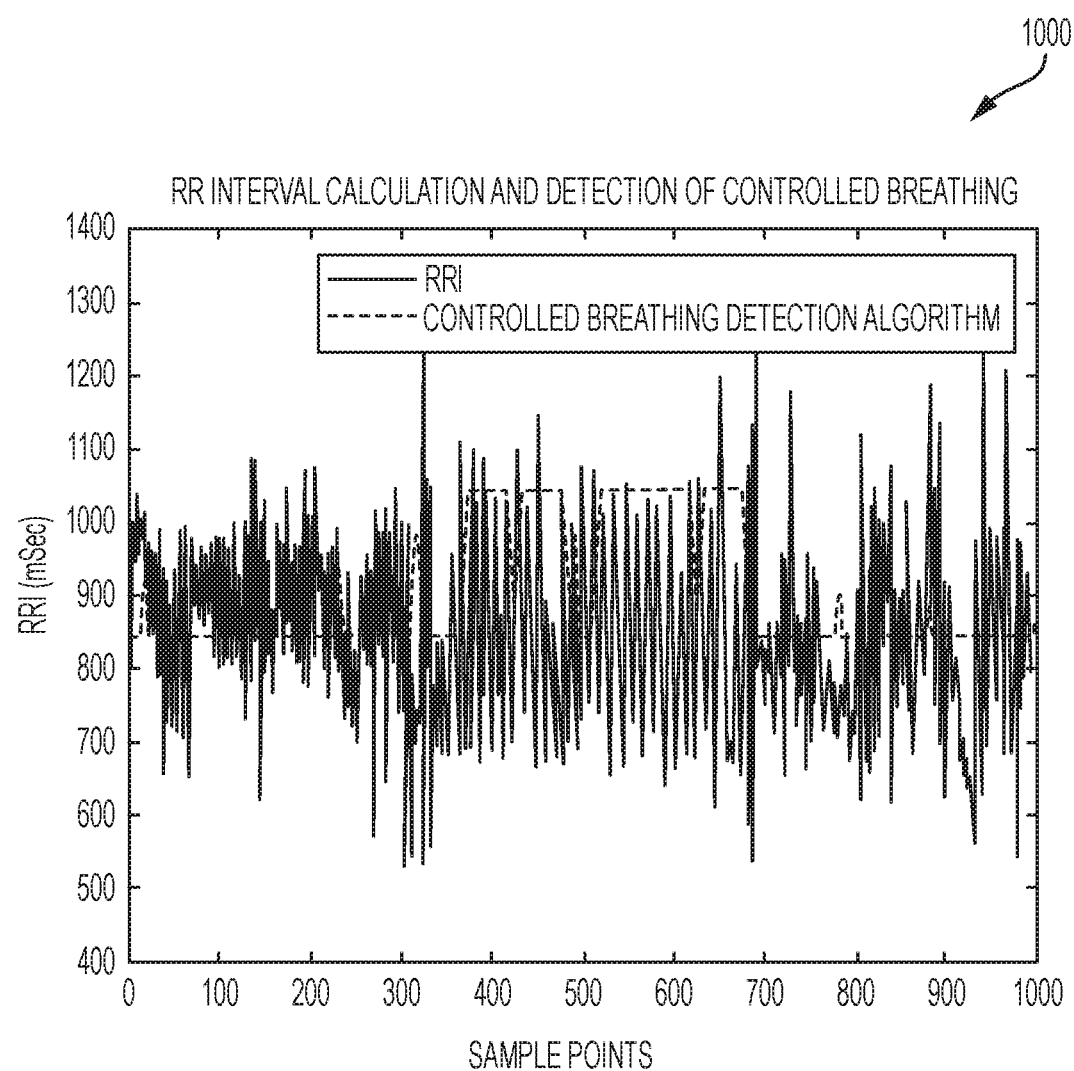
FIG. 21 is a plot of RRi vs. time collected by a user wearing a PPG sensor module having an inertial sensor, according to some embodiments of the present invention.

A specific non-limiting example of the method of FIG. 20 is elucidated by FIG. 21. FIG. 21 is a plot 1000 of RRi vs. time collected by a user wearing a PPG sensor module at the wrist, wherein the PPG sensor module further comprises an inertial sensor (in this case an accelerometer). The user started the test with uncontrolled breathing, and at ~360 seconds the user was instructed to start controlled breathing at 6 breaths a minute (0.1 Hz). In this case, the RRi-vs.-time information was generated in "real-time" by processing the raw PPG signal to determine the peak-to-peak (or valley-to-valley) points in time, in a pulse-picking fashion, as RRi-vs.-time may develop a pronounced periodic characteristic during controlled breathing. Thus, there is some inherent latency in generating the RRi information, as each pulse wave must be analyzed by this technique before a pulse is identified in time. The time between pulses was processed as an RR-interval (RRi) and thus a stream of successive RR-intervals was processed in time and smoothed, using a smoothing algorithm (in this case a moving average filter) to help remove unwanted noise artifacts (such as motion-noise, environmental-noise, and electrical-noise), generating a smoothed RRi waveform. The derivative of the smoothed RRi waveform was then calculated to generate an RRi-derivative waveform, and positive-to-negative zero-crossings of the derivative waveform were recorded to indicate peaks in the RRi waveform in time. For controlled breathing at 6 breaths/minute, the periodic time between RRi peaks should be close to 10 seconds, and for uncontrolled breathing, the time between peaks is likely to be much smaller and/or aperiodic (i.e., not periodic). Thus, the time-between-peaks information was fed to a controlled breathing detection algorithm, where the signal output of the detection algorithm was incremented when the time between peaks was between 7 and 13 seconds and decremented otherwise. There was also a maximum value by which the detection signal output was capped and a minimum value by which the detection signal output was floored.

It should be noted that the algorithm may have additional intelligence to change the "time between peaks" depending on the guided breathing rate. For example, if the guided controlled breathing is selected at 4 breaths per minute, then the signal output of the detection algorithm may be incremented when the time between peaks is between ~14 and ~17 seconds (as there are 15 seconds for each full breath in such case). Additionally, the breathing rate may be autonomously detected via a breathing rate detection algorithm (such as that described and referenced earlier) and then the "time between peaks" may be autonomously adjusted according to the detected breathing rate.

The controlled breathing detection algorithm output for this dataset is presented in FIG. 21, showing maximum values in the time periods between ~380 and ~680 seconds. The algorithm of FIG. 20 was tuned to report controlled breathing (to report a controlled breathing flag) when a predefined percentage of this maximum value was reached, in this case 70% of maximum value, reporting the onset of controlled breathing at 375 seconds. Moreover, to prevent potential vacillation in reporting, the report of controlled breathing was continued (the flag was kept high) until unless more than 20 seconds passed with the detection signal output below the predefined percentage of maximum value (75% of maximum). Thus, controlled breathing was reported from ~375 seconds to ~680 seconds, as shown in FIG. 21. It should be noted that during the entire data collection period, the accelerometer readings from the PPG sensor module were monitored to determine if the activity level of the person was too high to trust the RRi readings. In such case, a flag would be generated to enable a processor to discount erroneous RRi data. In this particular dataset, the flag was always "0", as there was no substantial physical activity detected.

Additionally, the identification of low activity was used to determine that the subject was truly in a state of rest suitable for enabling the subject to enter a state of controlled breathing. In one embodiment of the present invention, the determination that a subject is in a state of controlled breathing, leveraging biometric and activity sensing during the duration of the breathing session, may comprise the combination of: a) determining that the user's RRi-vs.-time plot is periodic in a manner that is consistent with controlled breathing (as described earlier), and b) determining that the person's activity state is at relative rest by sensing relatively low levels of motion (such as low accelerometry counts) and/or sensing that the user is at a seated or supine position (such as via body position sensing).

The RRi data shown in FIG. 21 can be further processed to generate a physiological assessment for the user. Numerous types of physiological assessments may be generated by processing RRi+physical activity information collected over a period of time, such as cardiovascular assessments, cardiac assessments, stress assessments, or the like. More specific examples of such assessments may comprise the identification of: arrhythmia, atrial fibrillation, fatigue, $VO_2$max, lactic threshold, or the like. Specific examples of generating a physiological assessment based on RRi data are presented in FIGS. 22A, 22B and 23.

FIG. 22A shows a Poincaré plot 1100 (a type of recurrence plot) comprising successive RR-intervals of FIG. 21 plotted against each other. Ellipses can be fit upon the data points for controlled and uncontrolled breathing 1102, 1104, as shown in FIG. 22A and emphasized in the break-out diagram of FIG. 22B. The ellipses may be defined by characteristic standard deviations, SD1 and SD2, along the minor and major axes of the ellipses for controlled breathing ("CB") and uncontrolled breathing ("UCB"). In general, SD2 may be more closely related with long-term variability in the RR-intervals and may reflect primarily sympathetic activity of the autonomic nervous system (the magnitude of SD2 is inversely related to sympathetic activity level), whereas SD1 may be more closely related with the short-term variability in the RR-intervals and reflects primarily parasympathetic activity of the autonomic nervous system (the magnitude of SD1 is directly related to parasympathetic activity level). The higher SD2 for controlled breathing (SD2CB) compared with the lower SD2 for uncontrolled breathing (SD2UCB) may be associated with a higher state of relaxation and lower stress for controlled breathing (when compared to uncontrolled breathing), showing that controlled breathing was able to bring the user to a state of lower stress.

Thus, the physiological assessment generated for the user may be that the user was originally in a higher stressed state (during uncontrolled breathing) that was corrected or at least ameliorated by a session of controlled breathing. More generally, physiological assessments may be generated for the user by processing the controlled breathing statistical parameters in comparison to the uncontrolled breathing statistical parameters, thereby generating physiological assessment parameters that may be processed via algorithms to generate physiological assessments.

A key benefit of factoring both controlled and uncontrolled breathing statistical parameters in generating physiological assessments is that the assessments may then be less dependent on external variables, rather than to health conditions, that may also affect SD1 and SD2. For example, a user who is fatigued from excessive exercise may have a lower SD1 and SD2 on the 3rd day than the 1st day due to a fatigue- or recovery-induced drop in HRV following excessive exercise on the 2nd day. However, in this case, the $SD1_{CB}/SD1_{UCB}$ or $SD2_{CB}/SD2_{UCB}$ ratio may not change as long has the health condition has not changed. This is because the ratio $SD1_{CB}/SD1_{UCB}$ or $SD2_{CB}/SD2_{UCB}$ may be effectively normalized such that the influence of day-to-day, non-health-related, variability on physiological assessments can be lessened. In this manner, true health conditions can be exposed as the user moves from uncontrolled to controlled breathing. Some non-limiting examples of such physiological assessment parameters and potential assessments are summarized in the table 1300 of FIG. 24. The term "average", as used in the table 1300, generally refers to an average value of a group of users having similar demographics with the user under test.

As specific example of visually presenting the physiological assessment of a user, in context of methods presented in FIG. 18 and FIG. 19, is presented in FIG. 23. The visual display 1200 may summarize the user's Poincaré plot, common shapes of the Poincaré plots (referred to as "Poincaré shapes"), and a description of what the user's Poincaré shape means. The identification of the user's Poincaré shape on the plot 1200 may be achieved by implementing a pattern recognition algorithm, a statistical analysis algorithm, or the like as processed by a processor, such as a processor 40, 40' in the system of FIG. 6 or FIG. 7. A comet shape 1202 may be indicative of good health, a torpedo shape 1204 may be indicative of poor cardiovascular health or a particular disease condition, and a fan shape 1206 may be indicative of atrial fibrillation, arrhythmia, or another cardiac issue. In some cases, the user's shape may be unknown (represented in FIG. 23 by 1208) to the identification algorithm, and in such case the system of FIG. 6 or FIG. 7 may initiate a search through a plurality of different users' data to find similar plots via a correlational algorithm running on a processor. Moreover, once similar plots are found among a group of users, commonalities between meta data and/or associated heath data of the users may be identified by a processor to help diagnose the particular user of interest. For example, if it is found that a group of users sharing a common Poincaré shape with the user of interest shows a high correlation with a diagnosis of diabetes (i.e., the meta data for this group and/or processed sensor data shows this group to be generally diabetic), then a notice may given (i.e., visually and/or audibly) to the user of interest, or to someone monitoring the user of interest, that the user may be at risk of being diabetic.

Example embodiments are described herein with reference to block diagrams and flowchart illustrations. It is understood that a block of the block diagrams and flowchart illustrations, and combinations of blocks in the block diagrams and flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and flowchart block or blocks, and thereby create means (functionality) and/or structure for implementing the functions/acts specified in the block diagrams and flowchart blocks.

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and flowchart blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/BluceRay).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the block diagrams and flowchart blocks. Accordingly, embodiments of the present invention may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and block diagrams may be separated into multiple blocks and/or the functionality of two or more blocks of the flowcharts and block diagrams may be at least partially integrated. Finally, other blocks may be added/inserted between the blocks that are illustrated. Moreover, although some of the diagrams include arrows on communication paths to show a primary direction of communication, it is to be understood that communication may occur in the opposite direction to the depicted arrows.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A method of generating a blood pressure assessment of a subject, the method comprising:
   guiding the subject into a state of controlled breathing;
   sensing physical activity information via at least one monitoring device worn by the subject;
   sensing biometric information via the at least one monitoring device by monitoring RR-intervals in an electrocardiogram or a photoplethysmogram of the subject;
   processing both the physical activity information and biometric information to determine that the subject is in the state of controlled breathing and to subsequently generate the blood pressure assessment while the subject is in the state of controlled breathing;
   providing feedback to the subject related to the blood pressure assessment; and wherein determining that the subject is in the state of controlled breathing comprises processing both the physical activity and the biometric information to determine that the subject is at a state of low activity suitable for controlled breathing and that peaks in the RR-intervals for the subject are characteristic of respiratory sinus arrhythmia.

2. The method of claim 1, wherein guiding the subject into a state of controlled breathing comprises providing the subject with audible and/or visual instructions.

3. The method of claim 1, wherein guiding the subject into a state of controlled breathing comprises providing the subject with audible and/or visual instructions via an electronic device.

4. The method of claim 1, wherein providing feedback to the subject related to the blood pressure assessment comprises providing the subject with audible and/or visual feedback.

5. The method of claim 1, wherein the at least one monitoring device comprises a PPG sensor, an ECG sensor, an auscultatory sensor, a piezoelectric sensor, a ballistogram sensor, or a bioimpedance sensor.

6. The method of claim 1, wherein the sensing physical activity information via the at least one monitoring device comprises sensing a distance traveled by the subject, a speed of the subject, an acceleration of the subject, a cadence of the subject, a pace of the subject, or a gait of the subject.

* * * * *